US012661486B1

(12) United States Patent
Jaroch et al.

(10) Patent No.: US 12,661,486 B1
(45) Date of Patent: Jun. 23, 2026

(54) SYSTEMS AND METHODS TO SENSE CHARACTERISTICS OF A THERAPEUTIC AGENT IN VIVO

(71) Applicant: TriSalus Life Sciences, Inc., Westminster, CO (US)

(72) Inventors: David Benjamin Jaroch, Arvada, CO (US); Bryan Foster Cox, Spring Grove, IL (US); Michael Bojanowski, Denver, CO (US)

(73) Assignee: TriSalus Life Sciences, Inc., Westminster, CO (US)

( * ) Notice: Subject to any disclaimer, the term of this patent is extended or adjusted under 35 U.S.C. 154(b) by 868 days.

(21) Appl. No.: 17/210,436

(22) Filed: Mar. 23, 2021

Related U.S. Application Data

(63) Continuation-in-part of application No. 16/431,547, filed on Jun. 4, 2019.

(60) Provisional application No. 63/074,411, filed on Sep. 3, 2020, provisional application No. 63/101,211, filed on Mar. 30, 2020, provisional application No. 63/101,221, filed on Mar. 30, 2020.

(51) Int. Cl.
| | |
|---|---|
| *A61M 25/10* | (2013.01) |
| *A61B 17/12* | (2006.01) |
| *A61M 25/00* | (2006.01) |

(52) U.S. Cl.
CPC ......... *A61M 25/10* (2013.01); *A61B 17/1204* (2013.01); *A61B 17/12109* (2013.01); *A61B 17/12136* (2013.01); *A61M 2025/0002* (2013.01); *A61M 2025/1052* (2013.01); *A61M 2205/3306* (2013.01); *A61M 2230/20* (2013.01)

(58) Field of Classification Search
CPC ........ A61B 17/12022; A61B 17/12109; A61B 17/12136; A61B 17/1204; A61B 17/12036; A61B 17/12031; A61M 25/104; A61M 25/10
See application file for complete search history.

(56) References Cited

U.S. PATENT DOCUMENTS

| | | | |
|---|---|---|---|
| 3,551,556 | A | 12/1970 | Kliment et al. |
| 3,946,734 | A | 3/1976 | Dedrick et al. |
| 4,261,341 | A | 4/1981 | Hakim et al. |
| 4,311,587 | A | 1/1982 | Nose et al. |

(Continued)

FOREIGN PATENT DOCUMENTS

| | | |
|---|---|---|
| CN | 101449987 A | 6/2009 |
| CN | 103260547 A | 8/2013 |

(Continued)

OTHER PUBLICATIONS

U.S. Appl. No. 17/375,779, filed Jul. 14, 2021, Arepally et al.

(Continued)

*Primary Examiner* — Scott J Medway
(74) *Attorney, Agent, or Firm* — Wan Chieh Lee; Haug Partners LLP

(57) ABSTRACT

Systems and methods are provided for delivering a therapeutic agent to a target tissue via a vessel and sensing, in vivo, a characteristic of the therapeutic agent in the vessel. The characteristic indicates a concentration of the therapeutic agent in the vessel. The system preferably includes an occluder. The method preferably includes infusing the therapeutic agent distal of the occluder while the occluder is in an expanded configuration in the vessel.

15 Claims, 12 Drawing Sheets

(56)                References Cited

U.S. PATENT DOCUMENTS

| | | | |
|---|---|---|---|
| 4,655,771 A | 4/1987 | Wallsten | |
| 4,714,460 A | 12/1987 | Calderon | |
| 4,738,740 A | 4/1988 | Pinchuk et al. | |
| 4,800,016 A | 1/1989 | Yang | |
| 4,840,542 A | 6/1989 | Abbott | |
| 4,883,459 A | 11/1989 | Calderon | |
| 4,892,518 A | 1/1990 | Cupp | |
| 5,024,668 A | 6/1991 | Peters | |
| 5,030,199 A | 7/1991 | Barwick et al. | |
| 5,071,407 A | 12/1991 | Termin et al. | |
| 5,084,015 A | 1/1992 | Moriuchi | |
| 5,171,299 A | 12/1992 | Heitzmann | |
| 5,234,425 A | 8/1993 | Fogarty et al. | |
| 5,397,307 A | 3/1995 | Goodin | |
| 5,397,308 A | 3/1995 | Ellis | |
| 5,411,478 A | 5/1995 | Stillabower | |
| 5,419,763 A | 5/1995 | Hildebrand | |
| 5,484,399 A | 1/1996 | Diresta | |
| 5,484,412 A | 1/1996 | Pierpont | |
| 5,496,277 A | 3/1996 | Termin et al. | |
| 5,599,301 A | 2/1997 | Jacobs et al. | |
| 5,607,466 A | 3/1997 | Imbert et al. | |
| 5,668,237 A | 9/1997 | Popall | |
| 5,688,237 A | 11/1997 | Rozga et al. | |
| 5,725,571 A | 3/1998 | Imbert et al. | |
| 5,755,687 A | 5/1998 | Donlon | |
| 5,755,769 A | 5/1998 | Richard et al. | |
| 5,759,205 A | 6/1998 | Valentini | |
| 5,795,325 A | 8/1998 | Valley et al. | |
| 5,810,789 A | 9/1998 | Powers | |
| 5,836,905 A | 11/1998 | Lemelson et al. | |
| 5,836,967 A | 11/1998 | Schneider | |
| 5,893,869 A | 4/1999 | Barnhart et al. | |
| 5,895,399 A | 4/1999 | Barbut et al. | |
| 5,897,567 A | 4/1999 | Ressemann et al. | |
| 5,910,154 A | 6/1999 | Tsugita et al. | |
| 5,911,734 A | 6/1999 | Tsugita et al. | |
| 5,957,974 A | 9/1999 | Thompson et al. | |
| 6,001,118 A | 12/1999 | Daniel et al. | |
| 6,010,522 A | 1/2000 | Barbut et al. | |
| 6,027,520 A | 2/2000 | Tsugita et al. | |
| 6,042,598 A | 3/2000 | Tsugita et al. | |
| 6,051,014 A | 4/2000 | Jang | |
| 6,059,745 A | 5/2000 | Gelbfish | |
| 6,152,946 A | 11/2000 | Broome et al. | |
| 6,165,199 A | 12/2000 | Barbut | |
| 6,165,200 A | 12/2000 | Tsugita et al. | |
| 6,168,579 B1 | 1/2001 | Tsugita | |
| 6,179,851 B1 | 1/2001 | Barbut et al. | |
| 6,231,551 B1 | 5/2001 | Barbut | |
| 6,235,044 B1 | 5/2001 | Root et al. | |
| 6,258,120 B1 | 7/2001 | McKenzie et al. | |
| 6,306,074 B1 | 10/2001 | Waksman et al. | |
| 6,306,163 B1 | 10/2001 | Fitz | |
| 6,309,399 B1 | 10/2001 | Barbut et al. | |
| 6,361,545 B1 | 3/2002 | Macoviak et al. | |
| 6,371,969 B1 | 4/2002 | Tsugita et al. | |
| 6,371,971 B1 | 4/2002 | Tsugita et al. | |
| 6,383,206 B1 | 5/2002 | Gillick et al. | |
| 6,395,014 B1 | 5/2002 | Macoviak et al. | |
| 6,416,495 B1 | 7/2002 | Kriesel et al. | |
| 6,436,112 B2 | 8/2002 | Wensel et al. | |
| 6,443,926 B1 | 9/2002 | Kletschka | |
| 6,478,783 B1 | 11/2002 | Moorehead | |
| 6,485,456 B1 | 11/2002 | Kletschka | |
| 6,485,502 B2 | 11/2002 | Don Michael et al. | |
| 6,499,487 B1 | 12/2002 | McKenzie et al. | |
| 6,500,203 B1 | 12/2002 | Thompson et al. | |
| 6,520,183 B2 | 2/2003 | Amar | |
| 6,530,935 B2 | 3/2003 | Wensel et al. | |
| 6,533,800 B1 | 3/2003 | Barbut | |
| 6,537,294 B1 | 3/2003 | Boyle et al. | |
| 6,537,297 B2 | 3/2003 | Tsugita et al. | |
| 6,540,722 B1 | 4/2003 | Boyle et al. | |
| 6,551,303 B1 | 4/2003 | Van Tassel et al. | |
| 6,565,552 B1 | 5/2003 | Barbut | |
| 6,569,146 B1 | 5/2003 | Werner et al. | |
| 6,582,396 B1 | 6/2003 | Parodi | |
| 6,589,264 B1 | 7/2003 | Barbut et al. | |
| 6,592,546 B1 | 7/2003 | Barbut et al. | |
| 6,607,506 B2 | 8/2003 | Kletschka | |
| 6,620,148 B1 | 9/2003 | Tsugita | |
| 6,635,070 B2 | 10/2003 | Leeflang et al. | |
| 6,641,553 B1 | 11/2003 | Chee et al. | |
| 6,641,572 B2 | 11/2003 | Cherkassky | |
| 6,645,220 B1 | 11/2003 | Huter et al. | |
| 6,645,222 B1 | 11/2003 | Parodi et al. | |
| 6,645,223 B2 | 11/2003 | Boyle et al. | |
| 6,652,555 B1 | 11/2003 | Van Tassel et al. | |
| 6,652,556 B1 | 11/2003 | Van Tassel et al. | |
| 6,656,351 B2 | 12/2003 | Boyle | |
| 6,673,090 B2 | 1/2004 | Root et al. | |
| 6,676,682 B1 | 1/2004 | Tsugita et al. | |
| 6,689,150 B1 | 2/2004 | Van Tassel et al. | |
| 6,692,508 B2 | 2/2004 | Wensel et al. | |
| 6,692,509 B2 | 2/2004 | Wensel et al. | |
| 6,692,513 B2 | 2/2004 | Streeter et al. | |
| 6,695,813 B1 | 2/2004 | Boyle et al. | |
| 6,695,858 B1 | 2/2004 | Dubrul et al. | |
| 6,699,231 B1 | 3/2004 | Sterman | |
| 6,702,834 B1 | 3/2004 | Boylan et al. | |
| 6,706,053 B1 | 3/2004 | Boylan et al. | |
| 6,706,055 B2 | 3/2004 | Douk et al. | |
| 6,730,108 B2 | 5/2004 | Van Tassel et al. | |
| 6,743,196 B2 | 6/2004 | Barbut | |
| 6,746,469 B2 | 6/2004 | Mouw | |
| 6,746,489 B2 | 6/2004 | Dua et al. | |
| 6,802,317 B2 | 10/2004 | Goebel et al. | |
| 6,818,006 B2 | 11/2004 | Douk et al. | |
| 6,830,579 B2 | 12/2004 | Barbut | |
| 6,837,898 B2 | 1/2005 | Boyle et al. | |
| 6,855,154 B2 | 2/2005 | Abdel-Gawwad | |
| 6,866,677 B2 | 3/2005 | Douk et al. | |
| 6,887,238 B2 * | 5/2005 | Jahns | A61B 18/1492 |
| | | | 606/41 |
| 6,887,258 B2 | 5/2005 | Denison et al. | |
| 6,896,690 B1 | 5/2005 | Lambrecht et al. | |
| 6,902,540 B2 | 6/2005 | Dorros et al. | |
| 6,908,474 B2 | 6/2005 | Hogendijk et al. | |
| 6,911,036 B2 | 6/2005 | Douk et al. | |
| 6,929,633 B2 * | 8/2005 | Evans | A61B 17/22 |
| | | | 604/509 |
| 6,936,060 B2 | 8/2005 | Hogendijk et al. | |
| 6,939,362 B2 | 9/2005 | Boyle et al. | |
| 6,964,670 B1 | 11/2005 | Shah et al. | |
| 6,964,673 B2 | 11/2005 | Tsugita et al. | |
| 6,974,469 B2 | 12/2005 | Broome et al. | |
| 6,989,027 B2 | 1/2006 | Allen et al. | |
| 6,997,898 B2 | 2/2006 | Forman | |
| 7,044,958 B2 | 5/2006 | Douk et al. | |
| 7,044,966 B2 | 5/2006 | Svanidze et al. | |
| 7,066,946 B2 | 6/2006 | Douk et al. | |
| 7,101,396 B2 | 9/2006 | Artof et al. | |
| 7,108,680 B2 * | 9/2006 | Rohr | A61B 5/14503 |
| | | | 604/151 |
| 7,118,600 B2 | 10/2006 | Dua et al. | |
| 7,162,303 B2 | 1/2007 | Levin et al. | |
| 7,169,164 B2 | 1/2007 | Borillo et al. | |
| 7,172,614 B2 | 2/2007 | Boyle et al. | |
| 7,172,621 B2 | 2/2007 | Theron | |
| 7,214,237 B2 | 5/2007 | Don Michael et al. | |
| 7,217,255 B2 | 5/2007 | Boyle et al. | |
| 7,223,253 B2 | 5/2007 | Hogendijk | |
| 7,232,452 B2 | 6/2007 | Adams et al. | |
| 7,232,453 B2 | 6/2007 | Shimon | |
| 7,241,304 B2 | 7/2007 | Boyle et al. | |
| 7,250,041 B2 | 7/2007 | Chiu et al. | |
| 7,252,675 B2 | 8/2007 | Denison et al. | |
| 7,279,000 B2 | 10/2007 | Cartier et al. | |
| 7,306,575 B2 | 12/2007 | Barbut et al. | |
| 7,322,957 B2 | 1/2008 | Kletschka et al. | |
| 7,326,226 B2 | 2/2008 | Root et al. | |
| 7,331,973 B2 | 2/2008 | Gesswein et al. | |
| 7,338,510 B2 | 3/2008 | Boylan et al. | |

(56)                References Cited

U.S. PATENT DOCUMENTS

| | | | |
|---|---|---|---|
| 7,344,549 B2 | 3/2008 | Boyle et al. | |
| 7,364,566 B2 | 4/2008 | Elkins et al. | |
| 7,371,249 B2 | 5/2008 | Douk et al. | |
| 7,425,215 B2 | 9/2008 | Boyle et al. | |
| 7,452,532 B2 | 11/2008 | Alt et al. | |
| 7,503,904 B2 | 3/2009 | Choi | |
| 7,537,600 B2 | 5/2009 | Eskuri | |
| 7,544,202 B2 | 6/2009 | Cartier et al. | |
| 7,572,272 B2 | 8/2009 | Denison et al. | |
| 7,582,100 B2 | 9/2009 | Johnson et al. | |
| 7,585,309 B2 | 9/2009 | Larson | |
| 7,591,832 B2 | 9/2009 | Eversull et al. | |
| 7,604,650 B2 | 10/2009 | Bergheim | |
| 7,647,115 B2 | 1/2010 | Levin et al. | |
| 7,653,438 B2 | 1/2010 | Deem et al. | |
| 7,658,747 B2 | 2/2010 | Forde et al. | |
| 7,686,781 B2 | 3/2010 | Vinten-Johansen | |
| 7,833,242 B2 | 11/2010 | Gilson et al. | |
| 7,842,084 B2 | 11/2010 | Bicer | |
| 7,846,139 B2 | 12/2010 | Zinn | |
| 7,853,333 B2 | 12/2010 | Demarais | |
| 7,873,417 B2 | 1/2011 | Demarais et al. | |
| 7,935,075 B2 * | 5/2011 | Tockman | A61N 1/057 |
| | | | 604/101.02 |
| 7,937,143 B2 | 5/2011 | Demarais et al. | |
| 7,938,799 B2 | 5/2011 | Epstein et al. | |
| 7,993,324 B2 | 8/2011 | Barbut | |
| 8,088,103 B2 * | 1/2012 | Teeslink | A61M 5/007 |
| | | | 604/101.03 |
| 8,162,879 B2 | 4/2012 | Hattangadi et al. | |
| 8,172,792 B2 | 5/2012 | Wang et al. | |
| 8,182,446 B2 | 5/2012 | Schaeffer et al. | |
| 8,185,186 B2 | 5/2012 | Ross et al. | |
| 8,200,312 B2 | 6/2012 | Degani et al. | |
| 8,251,948 B2 | 8/2012 | Goldman | |
| 8,257,384 B2 | 9/2012 | Bates | |
| 8,262,611 B2 | 9/2012 | Teeslink et al. | |
| 8,397,578 B2 | 3/2013 | Miesel | |
| 8,409,166 B2 | 4/2013 | Wiener et al. | |
| 8,500,775 B2 | 8/2013 | Chomas et al. | |
| 8,696,698 B2 | 4/2014 | Chomas et al. | |
| 8,696,699 B2 | 4/2014 | Chomas et al. | |
| 8,821,476 B2 | 9/2014 | Agah et al. | |
| 8,852,207 B2 | 10/2014 | Simpson et al. | |
| 9,023,010 B2 | 5/2015 | Chiu et al. | |
| 9,061,117 B2 | 6/2015 | Roberts et al. | |
| 9,078,982 B2 | 7/2015 | Lane et al. | |
| 9,089,341 B2 | 7/2015 | Chomas et al. | |
| 9,126,016 B2 | 9/2015 | Fulton | |
| 9,174,020 B2 | 11/2015 | Allen et al. | |
| 9,205,226 B2 | 12/2015 | Allen | |
| 9,265,914 B2 | 2/2016 | Fulton, III et al. | |
| 9,364,358 B2 | 6/2016 | Cohen et al. | |
| 9,457,171 B2 | 10/2016 | Agah et al. | |
| 9,463,304 B2 | 10/2016 | Agah et al. | |
| 9,474,533 B2 | 10/2016 | Mathis | |
| 9,539,081 B2 | 1/2017 | Chomas et al. | |
| 9,550,046 B1 | 1/2017 | Allen et al. | |
| 9,597,480 B2 | 3/2017 | Purdy et al. | |
| 9,604,037 B2 | 3/2017 | Fischer, Jr. et al. | |
| 9,737,693 B2 | 8/2017 | Helkowski | |
| 9,770,319 B2 | 9/2017 | Pinchuk et al. | |
| 9,844,383 B2 | 12/2017 | Allen | |
| 9,913,959 B2 | 3/2018 | Purdy et al. | |
| 9,968,740 B2 | 5/2018 | Pinchuk et al. | |
| 10,092,742 B2 | 10/2018 | Genstler et al. | |
| 10,130,762 B2 | 11/2018 | Allen | |
| 10,279,094 B2 | 5/2019 | Williams et al. | |
| 10,368,872 B2 | 8/2019 | Franklin et al. | |
| 10,512,761 B2 * | 12/2019 | Agah | A61M 25/1011 |
| 11,090,460 B2 | 8/2021 | Jaroch et al. | |
| 11,090,468 B2 | 8/2021 | Chappa | |
| 11,241,238 B2 | 2/2022 | Mohl | |
| 11,324,619 B1 | 5/2022 | Yacoby | |
| 11,400,263 B1 | 8/2022 | Arepally | |
| 11,633,192 B2 | 4/2023 | Johnson et al. | |
| 11,744,692 B2 | 9/2023 | Farago et al. | |
| 11,806,457 B2 | 11/2023 | Gerber et al. | |
| 12,290,564 B2 | 5/2025 | Agah et al. | |
| 2001/0041862 A1 | 11/2001 | Glickman | |
| 2002/0042593 A1 | 4/2002 | Mickley et al. | |
| 2002/0161394 A1 | 10/2002 | Macoviak et al. | |
| 2002/0165582 A1 | 11/2002 | Porter et al. | |
| 2003/0097114 A1 | 5/2003 | Ouriel et al. | |
| 2003/0125790 A1 | 7/2003 | Fastovsky et al. | |
| 2003/0187474 A1 | 10/2003 | Keegan et al. | |
| 2003/0233115 A1 | 12/2003 | Eversull et al. | |
| 2004/0006305 A1 | 1/2004 | Hebert | |
| 2004/0054315 A1 | 3/2004 | Levin et al. | |
| 2004/0068288 A1 | 4/2004 | Palmer et al. | |
| 2004/0143185 A1 | 7/2004 | Zatezalo et al. | |
| 2004/0215142 A1 | 10/2004 | Matheis et al. | |
| 2004/0220511 A1 | 11/2004 | Scott et al. | |
| 2004/0220521 A1 | 11/2004 | Barbut | |
| 2004/0256584 A1 | 12/2004 | Zimmerling et al. | |
| 2004/0260333 A1 | 12/2004 | Dubrul et al. | |
| 2005/0004517 A1 | 1/2005 | Courtney et al. | |
| 2005/0010285 A1 | 1/2005 | Lambrecht et al. | |
| 2005/0015048 A1 * | 1/2005 | Chiu | A61M 25/10 |
| | | | 604/101.04 |
| 2005/0015112 A1 | 1/2005 | Cohn et al. | |
| 2005/0113798 A1 | 5/2005 | Slater | |
| 2005/0124971 A1 | 6/2005 | Koch et al. | |
| 2005/0148997 A1 | 7/2005 | Valley et al. | |
| 2005/0149112 A1 | 7/2005 | Barbut | |
| 2005/0226855 A1 | 10/2005 | Alt et al. | |
| 2005/0261759 A1 | 11/2005 | Lambrecht et al. | |
| 2006/0124140 A1 | 6/2006 | Forsell | |
| 2006/0167537 A1 | 7/2006 | Larsson et al. | |
| 2006/0173490 A1 | 8/2006 | LaFontaine et al. | |
| 2006/0177478 A1 | 8/2006 | Humes et al. | |
| 2006/0178695 A1 | 8/2006 | Decant et al. | |
| 2006/0200075 A1 | 9/2006 | Zadno-Azizi | |
| 2006/0263301 A1 | 11/2006 | Vernon | |
| 2006/0264898 A1 | 11/2006 | Beasley | |
| 2007/0106258 A1 | 5/2007 | Chiu | |
| 2007/0106324 A1 | 5/2007 | Garner et al. | |
| 2007/0129752 A1 | 6/2007 | Webler et al. | |
| 2007/0179590 A1 | 8/2007 | Lu et al. | |
| 2007/0186932 A1 | 8/2007 | Wondka et al. | |
| 2007/0239135 A9 | 10/2007 | Barbut | |
| 2008/0031740 A1 | 2/2008 | Miyazaki et al. | |
| 2008/0031962 A1 | 2/2008 | Boyan et al. | |
| 2008/0033341 A1 | 2/2008 | Grad | |
| 2008/0051758 A1 | 2/2008 | Rioux | |
| 2008/0097273 A1 | 4/2008 | Levin et al. | |
| 2008/0103523 A1 | 5/2008 | Chiu et al. | |
| 2008/0147007 A1 | 6/2008 | Freyman et al. | |
| 2008/0194996 A1 | 8/2008 | Kassab et al. | |
| 2008/0234796 A1 | 9/2008 | Dorn | |
| 2009/0012444 A1 | 1/2009 | Shuros et al. | |
| 2009/0012469 A1 | 1/2009 | Nita et al. | |
| 2009/0018498 A1 | 1/2009 | Chiu et al. | |
| 2009/0076409 A1 | 3/2009 | Wu et al. | |
| 2009/0088676 A1 | 4/2009 | Murata | |
| 2009/0177183 A1 * | 7/2009 | Pinkernell | A61M 25/00 |
| | | | 604/164.13 |
| 2009/0198321 A1 | 8/2009 | Sutermeister et al. | |
| 2009/0222035 A1 | 9/2009 | Schneiderman | |
| 2009/0234266 A1 | 9/2009 | Solomon et al. | |
| 2009/0234283 A1 | 9/2009 | Burton et al. | |
| 2009/0264819 A1 | 10/2009 | Diethrich et al. | |
| 2010/0168649 A1 | 7/2010 | Schwartz et al. | |
| 2010/0168785 A1 | 7/2010 | Parker | |
| 2010/0331815 A1 | 12/2010 | Alt | |
| 2011/0046542 A1 | 2/2011 | Evans et al. | |
| 2011/0218494 A1 | 9/2011 | Gerrans et al. | |
| 2011/0295203 A1 | 12/2011 | Hayes et al. | |
| 2011/0313318 A1 | 12/2011 | Rule et al. | |
| 2013/0079731 A1 | 3/2013 | Chomas et al. | |
| 2013/0116655 A1 | 5/2013 | Bacino et al. | |
| 2013/0197418 A1 | 8/2013 | Angheloiu et al. | |
| 2014/0052224 A1 | 2/2014 | Kassab et al. | |
| 2014/0073536 A1 | 3/2014 | Lin | |

(56) References Cited

U.S. PATENT DOCUMENTS

| | | |
|---|---|---|
| 2014/0378951 A1 | 12/2014 | Dye |
| 2016/0015508 A1 | 1/2016 | Chomas |
| 2016/0045316 A1* | 2/2016 | Braido ................. A61B 5/6847 |
| | | 623/2.38 |
| 2016/0074633 A1 | 3/2016 | Schaffner |
| 2016/0082178 A1 | 3/2016 | Agah et al. |
| 2016/0199544 A1 | 7/2016 | Lee et al. |
| 2016/0206798 A1* | 7/2016 | Williams ......... A61B 17/12172 |
| 2016/0235942 A1 | 8/2016 | Alt |
| 2016/0235950 A1 | 8/2016 | Murata |
| 2016/0249969 A1 | 9/2016 | Santoinanni et al. |
| 2017/0000493 A1 | 1/2017 | Boehm, Jr. et al. |
| 2017/0049946 A1 | 2/2017 | Kapur et al. |
| 2017/0050002 A1 | 2/2017 | Steffen et al. |
| 2017/0157370 A1 | 6/2017 | Agah |
| 2017/0166598 A1 | 6/2017 | Huang et al. |
| 2017/0173309 A1 | 6/2017 | Fischer, Jr. et al. |
| 2017/0189654 A1 | 7/2017 | Schwartz |
| 2017/0209666 A1 | 7/2017 | Quigley |
| 2017/0319820 A1 | 11/2017 | Johnson |
| 2017/0368306 A1 | 12/2017 | Tal et al. |
| 2018/0055620 A1 | 3/2018 | Chomas et al. |
| 2018/0116522 A1 | 5/2018 | Brenneman et al. |
| 2018/0125502 A1 | 5/2018 | Allen |
| 2018/0250456 A1 | 9/2018 | Nitzan et al. |
| 2018/0250469 A1 | 9/2018 | Pinchuk et al. |
| 2018/0263752 A1* | 9/2018 | Pinchuk ................. A61F 2/013 |
| 2018/0289464 A1 | 10/2018 | Kassab et al. |
| 2018/0315183 A1 | 11/2018 | Milioni De Carvalho et al. |
| 2018/0333563 A1 | 11/2018 | Agah et al. |
| 2019/0015630 A1 | 1/2019 | Franklin et al. |
| 2019/0046157 A1 | 2/2019 | Unser |
| 2019/0083705 A1 | 3/2019 | Allen |
| 2020/0038586 A1 | 2/2020 | Chomas |
| 2020/0078555 A1 | 3/2020 | Agah |
| 2020/0108239 A1 | 4/2020 | Arepally |
| 2020/0197720 A1 | 6/2020 | Otsu et al. |
| 2020/0205840 A1 | 7/2020 | Adawi |
| 2020/0261695 A1 | 8/2020 | Jaroch |
| 2020/0345976 A1 | 11/2020 | Kalt et al. |
| 2020/0383688 A1 | 12/2020 | Olson et al. |
| 2021/0244473 A1 | 8/2021 | Cook |
| 2021/0338976 A1 | 11/2021 | Jaroch |
| 2022/0296809 A1 | 9/2022 | Katsnelson |
| 2024/0090902 A1 | 3/2024 | Tal et al. |

FOREIGN PATENT DOCUMENTS

| | | |
|---|---|---|
| CN | 203107204 U | 8/2013 |
| CN | 105007973 A | 10/2015 |
| CN | 105208946 A | 12/2015 |
| CN | 108778149 | 11/2018 |
| CN | 208388680 | 1/2019 |
| DE | 8910603 U1 | 12/1989 |
| EP | 249338 | 12/1987 |
| EP | 0533511 A1 | 3/1993 |
| EP | 0554579 A1 | 8/1993 |
| EP | 0416662 B1 | 3/1996 |
| EP | 1226795 | 7/2002 |
| EP | 1527740 | 5/2005 |
| EP | 1743524 | 1/2007 |
| EP | 1803423 | 7/2007 |
| EP | 2359893 A1 | 8/2011 |
| FR | 2652267 A1 | 3/1991 |
| GB | 2020557 B | 11/1979 |
| JP | 2006051144 A | 2/2006 |
| JP | 2006523515 | 10/2006 |
| WO | WO-8905667 | 6/1989 |
| WO | 9902093 A1 | 1/1999 |
| WO | WO-199916382 | 4/1999 |
| WO | WO-199944510 A1 | 9/1999 |
| WO | WO-2000051675 | 9/2000 |
| WO | WO-200141679 | 6/2001 |
| WO | WO-200145592 | 6/2001 |
| WO | WO-200149215 A2 | 7/2001 |
| WO | WO-200197879 | 12/2001 |
| WO | 02055146 A1 | 7/2002 |
| WO | WO-2004043293 | 5/2004 |
| WO | 2004075776 A2 | 9/2004 |
| WO | WO-2005082447 | 9/2005 |
| WO | WO-201068946 | 6/2011 |
| WO | WO-2015148284 | 10/2015 |
| WO | WO-2015187196 | 12/2015 |
| WO | 2016149653 A2 | 9/2016 |
| WO | WO-2017004019 | 1/2017 |
| WO | 2019140381 | 7/2019 |

OTHER PUBLICATIONS

U.S. Appl. No. 17/671,296, filed Feb. 14, 2022, Arepally et al.
Chinese Office Action and Search Report dated Jan. 10, 2022 of Application No. 201980016342.3.
EP Search Report and Written Opinion of Application No. EP19739019 dated Sep. 17, 21.
Japanese Office Action dated Apr. 28, 2021 of Application No. 2020-082002.
Search Report and Written Opinion of Application No. PCT/US 19/54406 dated Jan. 6, 2020.
Canadian Office Action 2 dated Jun. 3, 2022 of Application No. 3,139,118.
Japanese Office Action dated May 10, 2022 of Application No. 2021-572025.
International Search Report and Written Opinion of Application No. PCT/US2020/034626 dated Aug. 26, 2020.
Allogenic Chimeric Antigen Receptor-Modified Cells for Adoptive Cell Therapy of Cancer, Marcus, Assaf et al., Mar. 24, 2014, Expert Opinion of Biological Therapy, vol. 14, Issue 7.
A Study of the Geometrical and Mechanical Properties of a Self-Expanding Metallic Stent Theory and Experiment, Dr. Michael R. Jedwab, Claude 0. Clerc, Journal of Applied Biomaterials, vol. 4, Issue 1, pp. 77-85, Spring 1993.
U.S. Appl. No. 61/266,068, filed Dec. 2, 2009, Chomas et al.
U.S. Appl. No. 61/382,290, filed Sep. 13, 2010, Chomas et al.
Catheter-Based Renal Sympathetic Denervation for Resistant Hypertension: a Multicentre Safety and Proof-of-principle Cohort Study, Krum et al., The Lancet, 2009.
Cannulation of the Cardiac Lymphatic System in Swine, Vazquez-Jiminez et al., European Journal of Cardio-thoracic Surgery 18 (2000) 223-232.
Development of Repeatable Microcatheter Access Port for Intra-arterial Therapy of Liver Cancer, Yasushi C:Ljkuoka et al., Cardiovasc Intervent Radial (2019) 42:298-303.
Embolization II, Scientific Session 11, JVIR, Mar. 27, 2012.
Embolization procedure lowers levels of "hunger hormone," leads to weight loss, EurekAlert Public Release, Mar. 7, 2013.
Estimation of Tumor Interstitial Fluid Pressure (TIFP) Noninvasively, Long Lian Liu et al., PLOS One I DOI:10.1371/ ournal.pone. 0140892 Jul. 28, 2016.
Finite Element Stent Design, M. De Beule, R. Van Impe, P. Verdonck, B. Verhegghe, Computer Methods in Biomechanics and Biomedical Engineering, 2005.
First-In-Man Study of Left Gastric Artery Embolization for Weight Loss, Nicholas Kipshidze et al., ACC.13, E2056, UACC Mar. 12, 2013, vol. 61, Issue 10.
Fusion Drug Delivery System-Novel Catheter/Stent Design for Targeted Drug Delivery, Gerschwind & Barnett, Non-Published US provisional patent application filed Sep. 17, 2007.
International Search Report and Written Opinion of Application No. PCT/US16/23723 dated Sep. 2, 2016.
International Search Report and Written Opinion of Application No. PCT/US19/13482 dated Jun. 10, 2019.
International Search Report of PCT/US18/22171 dated Aug. 3, 2018.
Left Gastric Embolization Leads to Weight Loss, Bariatric News, Owen Haskins, Dec. 4, 2013.

(56) References Cited

OTHER PUBLICATIONS

Long-Term Catheterization of the Intestinal Lymph Trunk and Collection of Lymph in Neonatal Pigs, Richard R. Uwiera et al., Journal of Visualized Experiments, Mar. 2016, 109, e53457.

Lymphangiography to Treat Postoperative Lymphatic Leakage: A Technical Review, Edward Wolfgang Lee, et al-, Korean Journal of Radiology 15(6), Nov./Dec. 2014.

Radiologic Placement of Side-hole Catheter with Tip Fixation for Hepatic Arterial Infusion Chemotherapy, Toshihiro Tanaka et al., J. Vasc Interv Radiol 2003: 14:63-68.

Renal Denervation as a Therapeutic Approach for Hypertension: Novel Implications for an Old Concept, Schlaich et at., Hypertension, Journal of the American Heart Association, 2009, 54:1195-1201.

Renal Sympathetic-Nerve Ablation for Uncontrolled Hypertension, Schlaich et al., The New England Journal of Medicine, 2009, pp. 932-934, Aug. 27, 2009.

RenovoCath™ RC120 The Future of Targeted Delivery, RenovoRx Inc., web brochure downloaded from Internet on Feb. 2, 2015).

Superselective Retrograde Lymphatic Duct Embolization for Management of Postoperative Lymphatic Leak, Bulent Arslan et al., Diagn Interv Radiol 2017; 23:379-380.

Bertone, Joseph J. "Basic pharmacological principles." 2011. World Small Animal Veterinary Association World Congress Proceedings. <https://www.vin.com/doc/?id=5189569> (Year: 2011).

* cited by examiner 32   30   18'   40'

20'          22'

12'

42'

16'

20'

22'

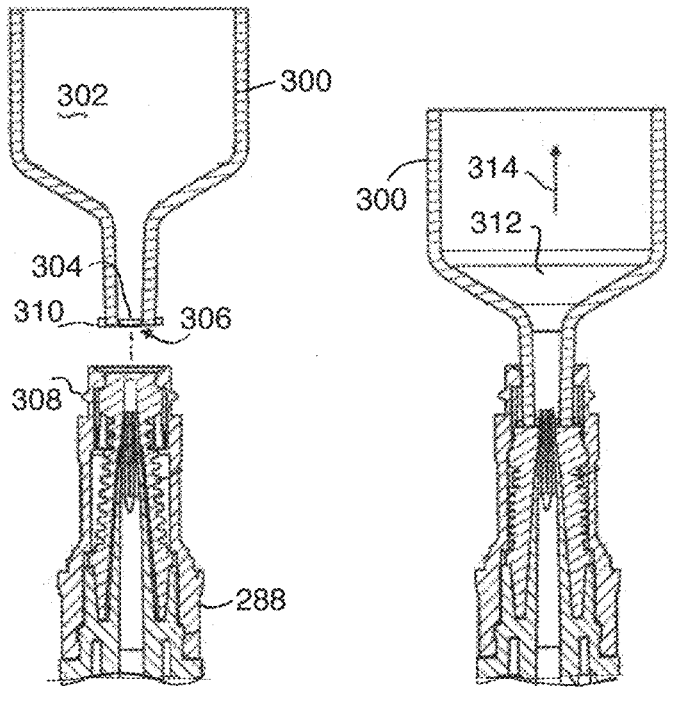
FIG. 8                    FIG. 9

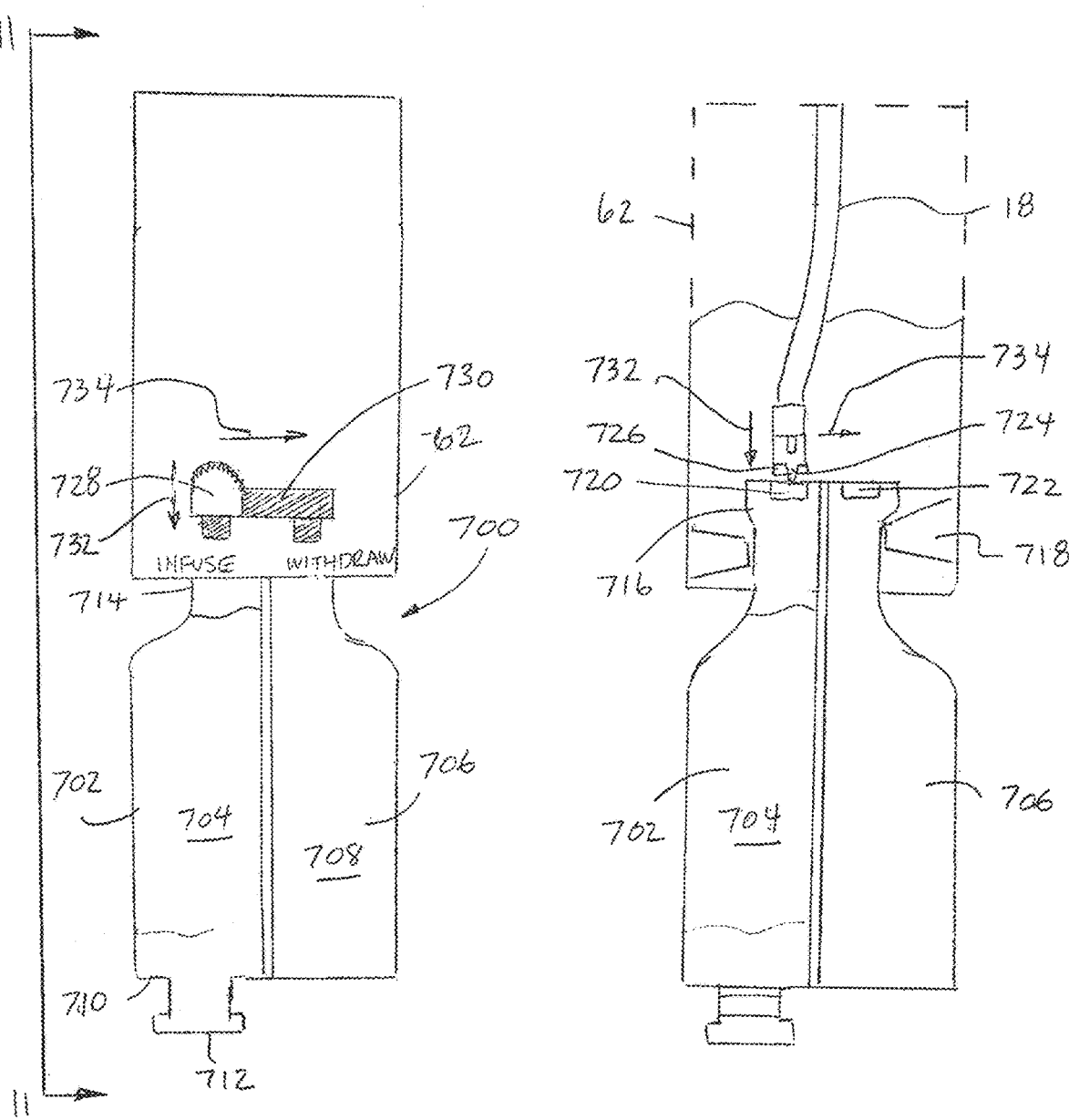
FIG. 10                    FIG. 11

SYSTEMS AND METHODS TO SENSE CHARACTERISTICS OF A THERAPEUTIC AGENT IN VIVO

CROSS-REFERENCE TO RELATED APPLICATIONS

This application claims benefit to U.S. Provisional Ser. No. 63/101,211, filed Mar. 30, 2020, U.S. Provisional Ser. No. 63/101,221, filed Mar. 30, 2020, and U.S. Provisional Ser. No. 63/074,411, filed Sep. 3, 2020; and is a continuation-in-part of U.S. Ser. No. 16/431,547, filed Jun. 4, 2019, which are hereby incorporated by reference herein in their entireties.

BACKGROUND OF THE INVENTION

1. Field

The present invention relates to catheter-based occlusive systems and intravascular methods to deliver a therapeutic agent for the treatment of disease.

2. State of the Art

Molecules residing within blood or other fluid filter through a vessel based on pressure differentials between the fluid within the vessel and the surrounding tissues. In the arterial side, pressure is typically higher within the vessel than the surrounding tissue interstitial pressure. This positive pressure gradient forces molecules out of the arterial end of the capillary bed and into the tissue. As blood travels though the vessel, pressure drops, reducing the positive pressure gradient. When no gradient is present, pressure mediated filtration of molecules though the vessel halts. On the venous side of the capillary bed, a negative gradient forms relative to the vessel, with the pressure forcing molecules from the tissue into the venous side capillaries and back into systemic circulation.

For example, on the arterial side, fluid exits arterial capillaries since the capillary hydrostatic pressure (by way of example, 35 mmHg) is greater than blood colloidal osmotic pressure (by way of example, 25 mmHg). Between the arterial and venous capillaries there is no net movement of fluid between the capillary and the surrounding tissue since capillary hydrostatic pressure (by way of example, 25 mmHg) is substantially equal to blood colloidal osmotic pressure (by way of example, 25 mmHg). Then, once the blood flows in the lower pressure venous capillaries, fluid re-enters the capillaries from the surrounding tissue via reabsorption since capillary hydrostatic pressure (by way of example, 18 mmHg) is less than blood colloidal osmotic pressure (by way of example, 25 mmHg).

It has been identified that mass exchange in blood vessels occurs, in part, due to differences in concentration of molecules in the blood relative to that in the tissue. The magnitude of the diffusive force is proportional to the difference in concentration of a therapeutic agent in the blood relative to that in the surrounding tissue.

In a clinical setting, therapeutic agents administered systemically diffuse into tissue at a relatively slow rate throughout all tissues connected to the systemic vascular network. This results in a wide dispersion of the therapeutic agent, and the diluted therapeutic agent has a low diffusion force. A very low concentration of the therapeutic agent is present in the volume of blood when the blood circulates through the target tissue. Moreover, cancerous tissues often have very high interstitial fluid pressure which prevents the therapeutic agent from diffusing from the blood into the tissue.

Further, after attempted treatment of cancerous tissues, the therapeutic agent which to be harmful to other body tissues is allowed to circulate through the other body vessels and organs where it may cause unintended harm.

SUMMARY

Systems and methods are provided to increase the diffusion rate of a therapeutic agent delivered through a controlled volume of a venous vasculature to a target tumor tissue.

In one method, a pressure gradient is generated within the controlled volume of the venous vasculature. The resulting change in pressure increases the volume of vessels experiencing a positive pressure gradient relative to the surrounding tissue, allowing diffusion of material from the blood vessel outward throughout the entire tissue volume. This effect takes place in tissues that normally have a negative pressure gradient where fluid and molecules filter from the tissue into the vasculature, enabling treatment of tissue on both the arterial and venous side. The duration and extent of diffusion can then be controlled by the duration the occlusive element is left in place. Pressure may be further modulated by injecting additional volume of fluid into the controlled volume of the venous vasculature to the occlusive element.

In another method, an osmotic pressure gradient is generated in the controlled volume, and the osmotic balance of the therapeutic agent in solution is controlled to facilitate outward diffusion of the therapeutic agent from the controlled volume into the surrounding target tissue.

In accord with the method, the venous volume is controlled by an occluding system and infusion system. The system includes a catheter defining a lumen opening at a distal end and an expandable vascular occluder provided at the distal end. The occluder can trap blood between the occluder and the higher pressure upstream arterial network to define the controlled venous volume. The system also includes a pressure sensor to monitor pressure in the venous volume.

The therapeutic agent in solution is injected into the controlled venous volume through the lumen of the catheter to displace the blood within the venous volume with the solution. The volume of displaced blood and tissue affected by the procedure is controllable by the placement of the expanded occluder and the volume of the infused solution.

If the occluder is positioned further downstream within the venous pathway (within larger veins), such will allow the occluder to occlude and isolate a larger volume of tissue and consequently require a larger volume of fluid displacement to fill the vascular network. If the occluder is positioned upstream within the venous pathway (toward the direction of the arteries), such will result in selective isolation of a smaller venous volume and will consequently require a reduced venous fluid displacement to fully replace the blood in the venous volume with the therapeutic agent.

The volume of the blood replaced within the isolated venous volume can be adjusted to control the extent to which the occluded volume is treated. Infused therapeutic agent will initially displace fluid (blood) in the downstream (venous) side of the occluded volume and will then further progress upstream, displacing fluid in order from veins, venules, capillaries, arterioles and then arteries. Treatment can be localized to a given structure of the vascular anatomy within a target tissue by adjustment of the total displacement volume of the therapeutic agent administered.

The solution is allowed to dwell in the venous volume for a period of time determined by a dwell function. The dwell function is correlated to the diffusion rate of the therapeutic agent out of the solution and into the target tissue so that an intended amount of therapeutic agent is diffused into the target tissue. In a method, a vascular pressure gradient is generated to increase diffusion during the dwell time. In a method, an osmotic gradient is generated to increase diffusion during the dwell time.

At the end of the dwell time, the occluder can be collapsed to allow blood flow to resume in an arterial-to-venous flow path through the venous volume; in such case, the remaining therapeutic agent in the venous volume is permitted to circulate systemically.

Alternatively, in accord with another aspect of the method, all or a portion of the remaining therapeutic solution in the controlled venous volume can be removed. The therapeutic agent is preferably removed via a parallel path to its infusion, such as through the lumen of the catheter or another lumen parallel to the lumen. Thus, in a preferred method, it is appreciated that the removal of the solution occurs through the same vessels through which the solution was injected. The solution can be withdrawn via effecting a reduced pressure at the removal lumen relative to pressure in the occluded venous volume. The rate of removal can be modified by adjusting the relative pressure differential. Further, the progress of removal is monitored at via one sensor located in the controlled venous volume. Then, after removal of at least a portion of the solution, the occluder is collapsed and the system is removed from the patient.

BRIEF DESCRIPTION OF THE DRAWINGS

FIGS. 8 and 9 show a fixed volume vacuum container and connector for removal of therapeutic agent solution from a patient in separated and connected configurations.

FIG. 10 is a schematic view of an embodiment of an integrated therapeutic agent delivery and retrieval device and a portion of a hub connector of a handle of a catheter delivery system;

FIG. 11 is a schematic view along line 11-11 in FIG. 10;

DETAILED DESCRIPTION OF THE PREFERRED EMBODIMENTS

With reference to the following description, the terms "proximal" and "distal" are defined in reference to a user of the device, with the term "proximal" being closer to the user's hand, and the term "distal" being further from the user such as to be located further within a body of the patient during use.

Apparatus and methods are described herein related to the use of a system to inject a therapeutic agent into a primary vessel communicating with a diseased tissue of an organ, for example, a tumor. The tumor to be treated can be a solid tumor. In some cases, the tumor can be a cancerous tumor, such as a tumor specific to, by way of example only, cancer of the pancreas, kidney, liver, lung, or uterus.

As described herein, a treatment system is used to provide a therapeutic agent into the diseased tissue by targeted infusion of the therapeutic agent into a region of the tissue. The diseased tissue can be any tissue that can be treated by administration of a local therapeutic. Diseased tissues can include cancerous tissues as well as non-cancerous dysfunctional organs. By way of example, a non-cancerous diseased condition treatable includes the symptoms of adrenal insufficiency of the adrenal glands, including, but not limited to, Addison's disease. Such symptoms of the adrenal glands may be treated with by gene therapy with viral vectors.

The therapeutic agent is injected into a region of an organ or other defined area of tissue served by one or more feeder arteries (or upstream or inflow vessels) and drained by one or more draining veins (or downstream or outflow vessels).

Figure 1:
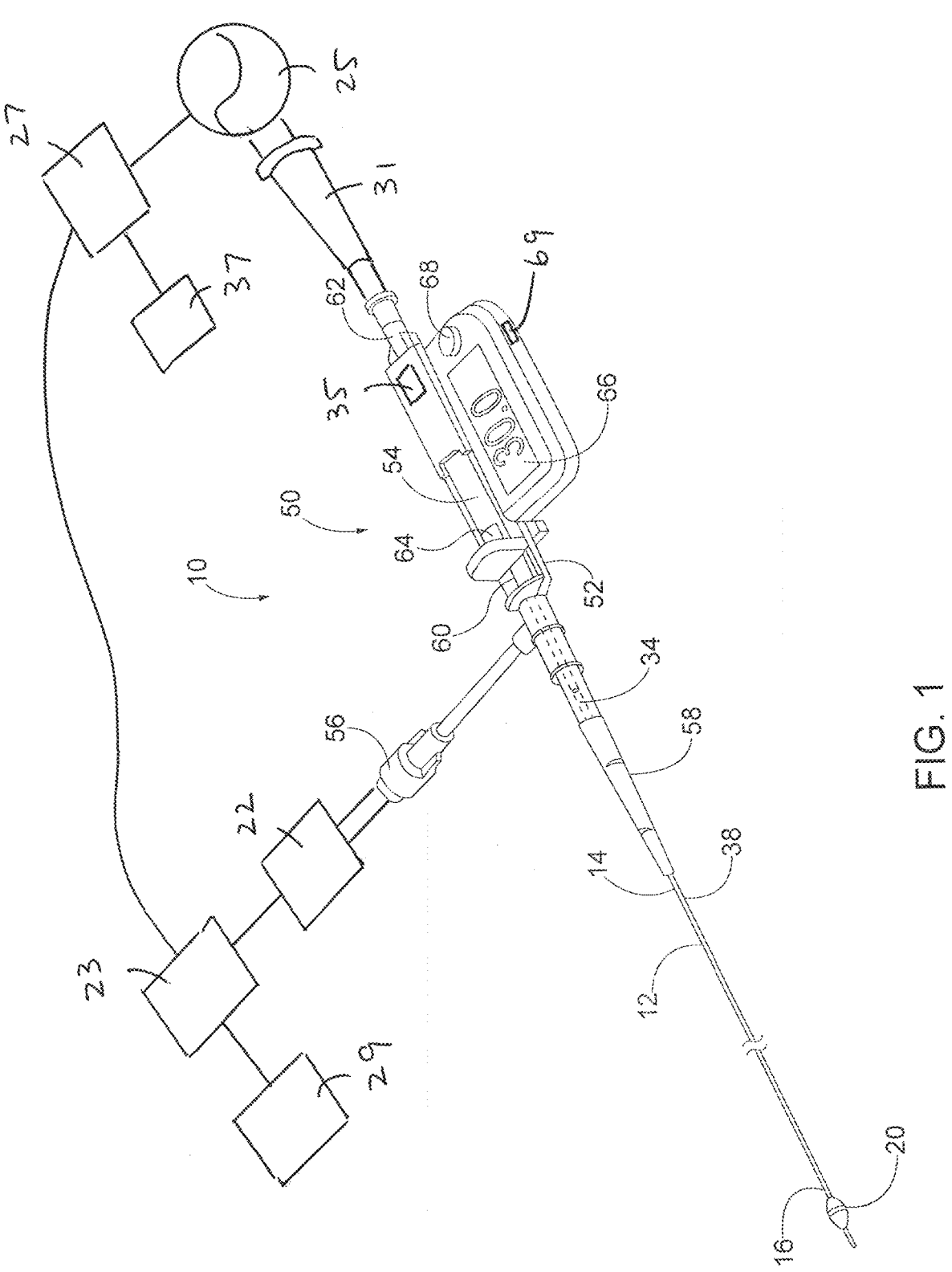
FIG. 1 is a perspective view of an occlusion system for use in a method described herein.
Figure 2:
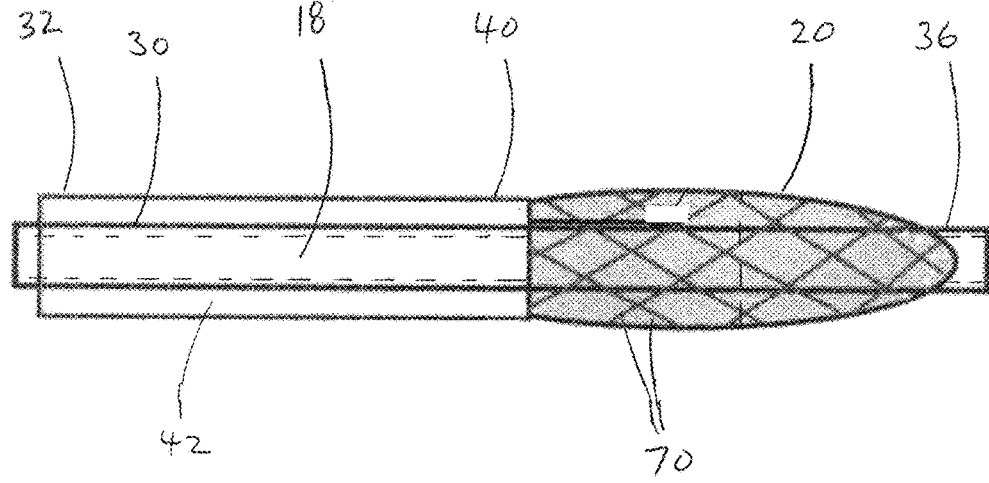
FIG. 2 is an enlarged distal end view of a first embodiment of an occlusion system in a collapsed configuration.

Turning now to FIGS. 1 and 2, an atraumatic vessel occlusive system 10 is shown. The system 10 includes a flexible tubular member 12 having a proximal end 14 a distal end 16. The tubular member 12 defines an infusion lumen 18 extending between its proximal and distal ends. A diametrically adjustable vessel occluder 20 is mounted at the distal end 16 of the tubular member. The system 10 also preferably includes at least one pressure sensor 22 located to be in pressure communication with a distal side of the vessel occluder. The pressure sensor 22 can be physically located at the distal side of the occluder 20, or can be communicate via a fluid pathway from a location on the proximal side of the occluder (e.g., located on the handle) to a location on the distal side of the occluder (an opening of a lumen or other fluid pathway defined by the tubular member 12, such as through side port 56 and between inner and outer catheters 30, 32, described below).

In an embodiment, the flexible tubular member 12 includes an inner catheter 30 telescopically advanceable within an outer catheter 32. The inner catheter 30 has a proximal end 34 and a distal end 36, and the outer catheter 32 also has a proximal end 38 and distal end 40. The infusion lumen 18 is preferably defined through the inner catheter 30 and opens to a distal axial orifice 84.

An actuation handle 50 is provided at the proximal ends 34, 38 of the inner and outer catheters 30, 32 to effect relative displacement of the thereof. The actuation handle 50 includes a stationary member 52 and a movable member 54, such as a slide longitudinally displaceable relative to the stationary member. The stationary member 52 is provided with a side port 56, and a strain relief 58 connects the proximal end 38 of the outer catheter 32 to the stationary member 52. The side port 56 is in fluid communication with the outer catheter 32 via flush lumen 42 defined between the inner and outer catheters 30, 32. The movable slide 54 is coupled to the inner catheter 30. A hypotube 60 is coaxially inserted around the proximal end of the inner catheter 34 to provide mechanical support of the inner catheter. The proximal end of the slide 54 defines an infusion port 62 that is fluidly coupled to the proximal end 34 of the inner catheter 30. The actuation handle 50 also includes a releasable lock 64 that, when actuated, can retain the movable member 54 and stationary member 62 in relatively fixed longitudinal positions. The handle 50 may also include a display 66 and associated memory and logic to permit the display of real-time and/or stored pressure data read from the pressure sensor 22. Button 68 near display 66 permits actuation of the logic and display as well as cycling through various logic functions. Additionally or alternatively, the handle 50 or one or more components of the system includes a physical or wireless interface 69 to connect the pressure transducer 22 to a pressure monitor 23 with a memory and logic, which is coupled to an outboard display 29 to display the recorded pressure, and a controller 27 for activating and deactivating an infusion pump 25, optionally based on the monitored pressure, to deliver the therapeutic agent at a flow rate from a syringe or other deliverable storage 31 to the infusion lumen 18 and to the patient. In some embodiments the system also includes a timer 37 coupled to the controller.

Figure 3:
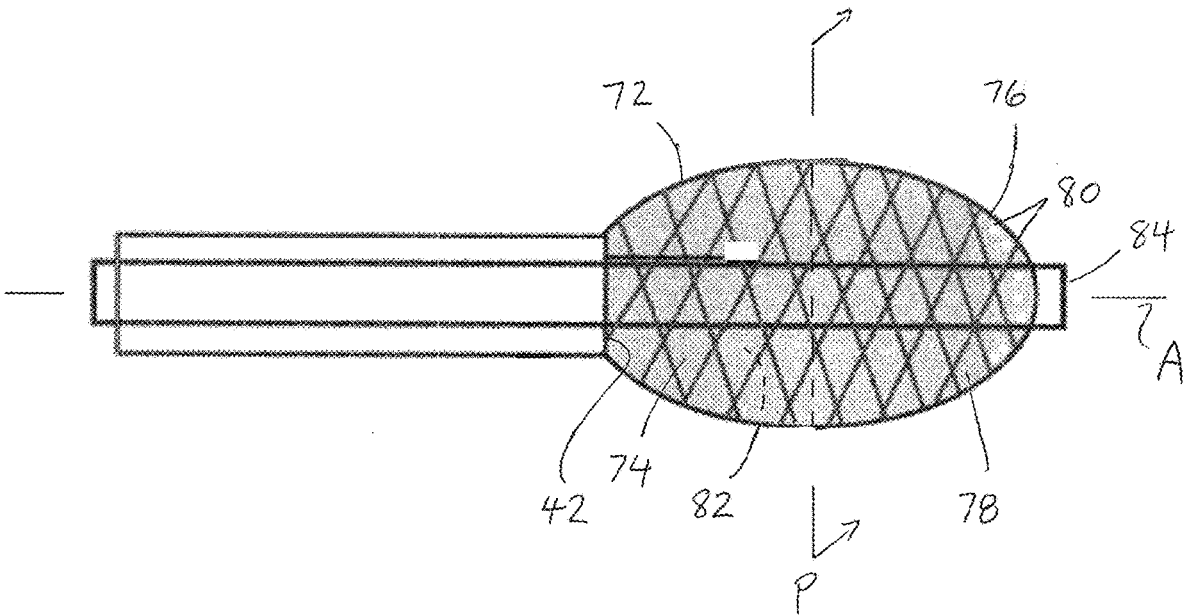
FIG. 3 is an enlarged distal end view of a first embodiment of an occlusion system in an expanded configuration.

In an embodiment, the occluder 20 is a microvalve comprising a braided construct of filaments 70. The proximal end of the filaments 70 are coupled to, and preferably rigidly fixed to, the distal end 40 of the outer catheter 32, and the distal end of the filaments 70 are coupled to, and preferably rigidly fixed to, the distal end 36 of the inner catheter 30. The general construct of the braided valve portion of such a microvalve device is described in detail in co-owned U.S. Pat. Nos. 8,696,698 and 9,770,319, both of which are hereby incorporated by reference herein in their entireties. Longitudinal displacement of the inner catheter 30 relative to the outer catheter 32 results in the microvalve moving between a first elongate ovoid configuration of smaller diameter (FIG. 2) adapted for guiding to a deployment location in a vessel, and a second squatter ovoid configuration of a larger diameter adapted for occlusion of the vessel (as shown in FIG. 3). That is, in both the first and second configurations, the microvalve is of an ovoid configuration and has a generally symmetrically shape about a longitudinal central axis A, and may also be symmetrical about a plane P orthogonal to the central axis A of the microvalve at its area of maximum diameter. It is recognized that the occluder can be moved through the first and second configurations, and any size of configuration therebetween to best suit the vessel in which it is used. The lock 64 on the handle 50 can facilitate retaining the occluder 20 in a desired size configuration during therapeutic treatment. The system 10 can be advanced in the first elongate configuration to a deployment location in a blood vessel over a guidewire (not shown) inserted through the infusion lumen 18 of the inner catheter 30.

In accord with one embodiment of the occluder 20, a fluid impermeable membrane 72 is provided over the proximal portion 74 of the braided construct. Suitable materials for the impermeable membrane include elastomeric natural and artificial rubbers, silicones, styrenics, olefinics, copolyesters, polyurethanes and polyamides. In accord with another aspect of the occluder, a fluid permeable coating or covering 76 is provided over a distal portion 78 of the braided construct. Suitable materials for the fluid permeable coating 76 include elastomeric natural and artificial rubbers, silicones, styrenics, olefinics, copolyesters, polyurethanes and polyamides processed so as to have micro or macro scale perforations, channels, pores, or fibrous rather than continuous morphology. This may be accomplished by physical perforation techniques, by electrospinning or melt spinning fibers, by inclusion of soluble components that can be removed during processing to leave pores or voids, and by the addition of open pore foaming agents or other suitable technology. The coating or covering 76 can include a material placed over the outer surface of the filaments 70, within the inner surface of the filaments, or a combination thereof. The coating or covering 76 can extend only between the filaments. The coating or covering 76 can be free-floating on the filaments or can be rigidly fixed to the filaments. The coating or covering 76 can be applied by dip coating, spraying, sewing, bonded application, or other suitable technology. The fluid permeable material 76 can be an otherwise impermeable material made permeable by perforations or apertures 80. The fluid permeable material may be formed with interstices or openings 80 providing a degree of permeability. The apertures, perforations, interstices, openings, etc. (collectively referred to hereinafter as 'apertures' 80) within the fluid permeable material may be geometrically arranged. The total cross-sectional surface area of the apertures should be sufficiently large so as to facilitate measurement of physiological response and infusion pressure while dampening short duration turbulent flow. Most preferably, apertures should be arranged in a radially symmetric fashion so as to maintain uniform radial bending properties of the device.

As the flush lumen 42 between the inner catheter 30 and outer catheter 32 is in fluid communication with the distal side of the occluder, the pressure sensor 22 may reside at the side port 56 to monitor pressure at the distal tip as long as the proximal infusion port is sealed (creating a closed pressure chamber in communication with the distal tip of the catheter). Sensor responsiveness within this chamber is governed by the cross-sectional surface area of the flush lumen 42 and by the distance between the sensor 22 and the distalmost aperture. The delay in pressure response time decreases with increasing cross-sectional area and decreasing length. For example, a device having a flush lumen with a cross-sectional area of 0.5 mm$^2$ and a sensor located 100 cm from the distal aperture will require 2-5 seconds to respond and stabilize to a change in pressure; whereas, a device having a flush lumen with a cross-sectional area of 0.5 mm$^2$ and a sensor located 50 cm from the distal aperture will require 1-3 seconds to respond and stabilize to a change in pressure; and whereas, a device having a flush lumen with a cross-sectional area of 2 mm$^2$ and a sensor located 100 cm from the distal aperture will require 0.1-0.5 seconds to respond and stabilize to a change in pressure. The proximity of the sensor is therefore governed by the duration of the physiological response intending to be monitored. For instance, the infusion of therapeutics may be administered over a range of time. For infusions occurring in seconds and having transient pressure changes, the sensor should be placed within a space of sufficient cross-sectional surface area and at a sufficiently short distance from the distal aperture so as to monitor pressure changes occurring within a second (or less). Moreover, the pores at the distal end of the filter should be sufficiently small and have a relatively low cross-sectional area so that pressure fluctuations on the order of 0.01-0.2 seconds are dampened while the sensor responds in the 0.2-1 second time frame.

The system may also be configured with a single catheter and a dynamic microvalve that automatically opens to the vessel wall when subject to retrograde pressure, as would be applied to a valve inserted into a vein from a downstream to upstream direction and subject to downstream blood flow from arterial to venous vessels. Such a dynamic microvalve are described in detail in co-owned U.S. Pat. Nos. 8,500,775; 8,696,698; 8,696,699; 9,959,081; and 9,808,332, which are hereby incorporated by reference herein in their entireties. Such systems also would include a pressure sensor, as described above. Such pressure sensor could be positioned on the distal side of the valve, on the catheter at the distal of the valve, or within the infusion lumen of the catheter.

Figure 4:
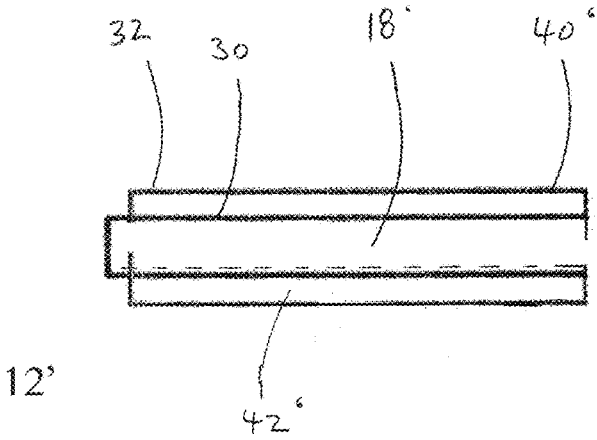
FIG. 4 is an enlarged distal end view of a second embodiment of an occlusion system in a collapsed configuration.
Figure 5:
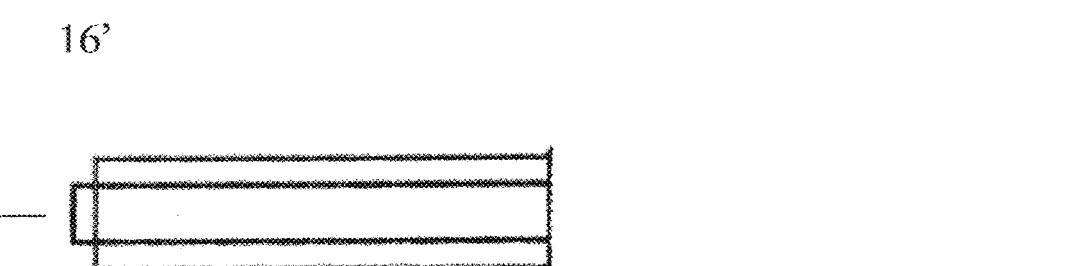
FIG. 5 is an enlarged distal end view of a second embodiment of an occlusion system in an expanded configuration.

Turning now to FIGS. 4 and 5, in accord with an alternate treatment system for use in a method, an atraumatic vessel occlusive system 10' includes a flexible tubular member 12' having a proximal end (as similarly shown in system 10) and a distal end 16'. The tubular member 12' is a catheter defining an infusion lumen 18' extending between its proximal and distal ends, and has an inflatable occlusion balloon 20' at its distal end 16'. The balloon 20' is made of a fluid impermeable material and may be elastic or inelastic. In a first collapsed configuration (FIG. 4), the balloon 20' has an elongate configuration suitable for being advanced through vasculature into a target vein; in a second expanded configuration (FIG. 5, in which the balloon is filled with a liquid or gas fluid via a second lumen of the catheter), the balloon 20' has a diameter sufficient to occlude blood flow out of the target vein. The system 10' also includes at least one pressure sensor 22' located to be in pressure communication with a distal side of the balloon 20'. As shown with respect to system 10, an infusion port is fluidly coupled to the proximal end of the tubular member 12'. The port may similarly include a display and associated memory and logic to permit the display of real-time and/or stored pressure data read from the pressure sensor 22'.

Figure 6:
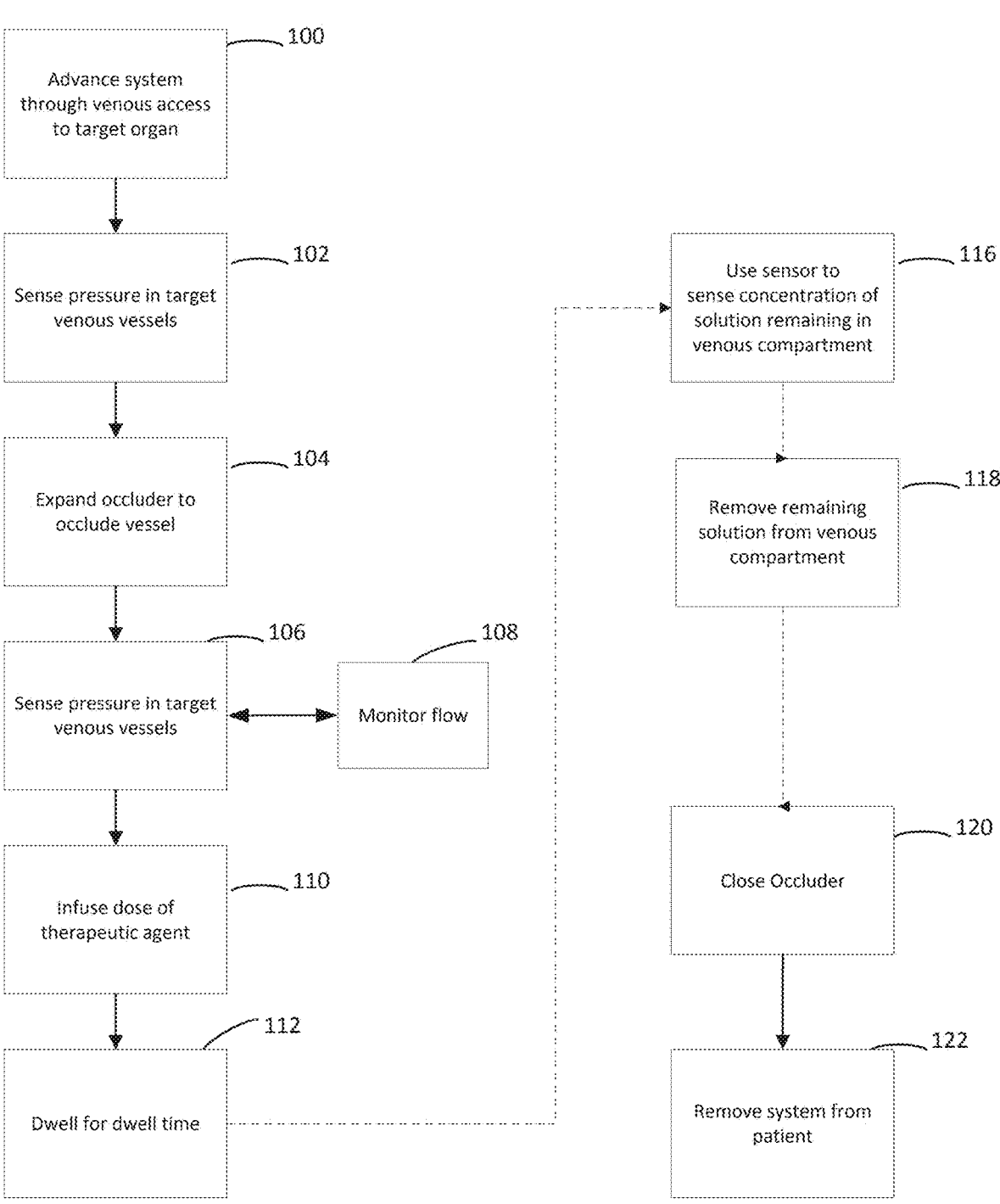
FIG. 6 is a flow chart of a method of using a system described herein.

Referring now to FIG. 6, in accord with a method of treatment, the distal end of the system 10 (hereafter referring to either treatment system 10 or 10') is advanced at 100 in the first elongate collapsed configuration to a target vein of an organ in accord with known procedures. In that manner, the system 10 can be tracked over a guidewire through the venous system to the intended location. The target vein is a vein or upstream branch of a vein receiving a return supply of blood from an organ; i.e., such that blood is naturally flowing away from the organ. By way of example, the organ can be the liver and the target vein can be the saphenous vein, or the organ can be pancreas and the target vein can be portal vein. Other organs can be similarly treated through an associated target vein. Further, the location within the target vein or one of its branches can be selected to modify therapeutic targeting. This permits treatment to be isolated to a specific vascular component or venous volume within the target tissue. The advantage is that, as the physical and biological structure of vessels is not necessarily consistent throughout the vascular compartment, therapeutic agents can be selected and delivered within vessels that will maximize absorbance of the therapeutic agent or minimize side effects in sensitive tissues.

If the occluder is positioned further downstream within the venous pathway (within larger veins), the expanded occluder can occlude and isolate a larger volume of tissue and consequently a larger volume of fluid displacement is required to fill the venous vascular network isolated by the occluder, as described below. If the occluder is positioned farther upstream within the venous pathway (toward the direction of the arteries in the organ), this will result in selective isolation of a smaller venous volume and will consequently require a reduced venous fluid displacement to fully replace the blood in the isolated venous volume with the therapeutic agent. (The terms 'venous volume' and 'venous compartment' are hereinafter used interchangeably to mean the venous volume downstream of arteries that is isolated by the occluder as a result of occlusion of a draining vein.)

Once the distal end 16 is delivered to the target vein, the pressure in the target vein is monitored and measured at 102 with the pressure sensor 22 at a first time.

The system 10 is then actuated to expand the occluder 20 at 104 to bring the outer surface of the occluder into apposition with the vessel wall and occlude the target tissue so that it is occluded or isolated venous volume. The occluded or isolated venous volume defines a venous compartment in which the blood is constrained from outflow from the target organ by the occluder 20 For systems 10 with microvalve occluder 20, the arterial side pressure in the venous compartment urges the occluder into an open, expanded configuration. The pressure in the venous compartment is sensed at second time at 106 via the pressure sensor 22 to confirm the expected pressure increase after expansion of the occluder 20. The pressure may be continually monitored at 108.

A therapeutic agent in solution is then infused through the catheter 12 and out of the distal orifice 84, distal of the occluder 20, and into the isolated venous compartment, at 110. The volume of therapeutic agent infused can be adjusted to control the extent of treatment within the isolated portion of the venous volume by the therapeutic agent. Infused therapeutic agent will initially displace fluid (blood) in the downstream (venous) side of the occluded volume and will then further progress upstream, displacing fluid in order from veins, venules, capillaries, arterioles and then to the feeding artery. Treatment can be localized to a given structure of the vascular anatomy within a target tissue by adjustment of the total displacement volume of the therapeutic agent administered. The solution is provided in a volume sufficient to displace at least a volume of blood in the venous compartment to allow the therapeutic agent to diffuse outward into the surrounding tissue during dwell time at 112 and have a therapeutic effect on the surrounding tissue.

The dwell time is preferably determined by a dwell function. The dwell function is adapted to optimize filtration of the therapeutic agent from the solution into the surrounding target tissue based on the differential between the pressures measured at the first and second times (i.e., i.e., normal pressure measured at 102 relative to occluded pressure measured at 106). With a larger pressure differential, a larger gradient is generated in the occluded venous compartment and a shorter dwell time is required for optimal diffusion of the therapeutic agent into the target tissue. With a smaller pressure differential, a lower gradient is generated in the venous compartment and a longer dwell time is required. The pressure may be continually monitored for all or a portion of the time the solution is retained within the venous compartment.

Under normal systemic circumstances, the molecules residing within the blood or other tissue fluid filter through a blood vessel based on pressure differentials between the fluid within the vessel and the surrounding tissues. In the arterial side, pressure is typically higher within the vessel than the surrounding interstitial tissue pressure. This positive pressure gradient forces molecules out of the arterial end of the capillary bed and into the tissue. As blood travels through the arterial vessel, pressure drops towards to the venous vessels, reducing the positive pressure gradient until no gradient is present and pressure mediated filtration of molecules through the vessel completely halts. On the venous side of the capillary bed a negative gradient is present, causing reabsorption of molecules back into the venous side capillaries and into systemic circulation. The change in pressure from the arterial side to the venous side is a result of difference in volume within the vessels in the direction of flow; the arterial side has less capacity than the venous side resulting in a pressure drop as blood flows from arteries to veins.

In accord with the system and method described herein, as the vein becomes blocked by expansion of the occluder 20 across the vein at 104, blood flow stops within the vein. Blood, being an incompressible fluid composed primarily of water, then equilibrates to the arterial side pressure.

The resulting change in pressure increases the volume of vessels experiencing a positive pressure gradient to the surrounding tissue, including venous vessels. This allows material to diffuse from the blood vessel outward throughout the entire tissue volume. The effect takes place in tissues that normally have a negative pressure gradient in which fluid and molecules would normally filter from the tissue into the venous vasculature. Thus, treatment of tissue on both the arterial and venous side is enabled. The duration and extent of the diffusion across the vessel wall and into the tissue can be controlled by the duration (dwell time) during which the occluder is left in the enlarged, occluding second configuration. Pressure may be further modulated by injecting one or more additional volumes of fluid into the venous network distal of the occluder. For example, one or more bolus injections of saline can be injected into the vessel to modify and increase uptake of the therapeutic agent.

More specifically, the system when in position is used to sense pressure in the vessel volume of the target tissue distal of the occluder. This permits confirmation that the pressure in this volume is increased relative to a baseline pressure. Then, a therapeutic agent is infused through the infusion lumen into the vessel volume.

In accord with one aspect of the method, the volume of therapeutic is infused in a volume sufficient to fill the intended venous volume but without overfilling, which would lead to non-target tissue exposure. It is desirable to prevent infused therapeutic from migrating through the arterial network to a vascular branch, which would result in the therapeutic agent entering systemic circulation. Therefore, the therapeutic agent is ideally infused in a volume sufficient to fully perfuse the target volume, but no more.

Figure 6A:
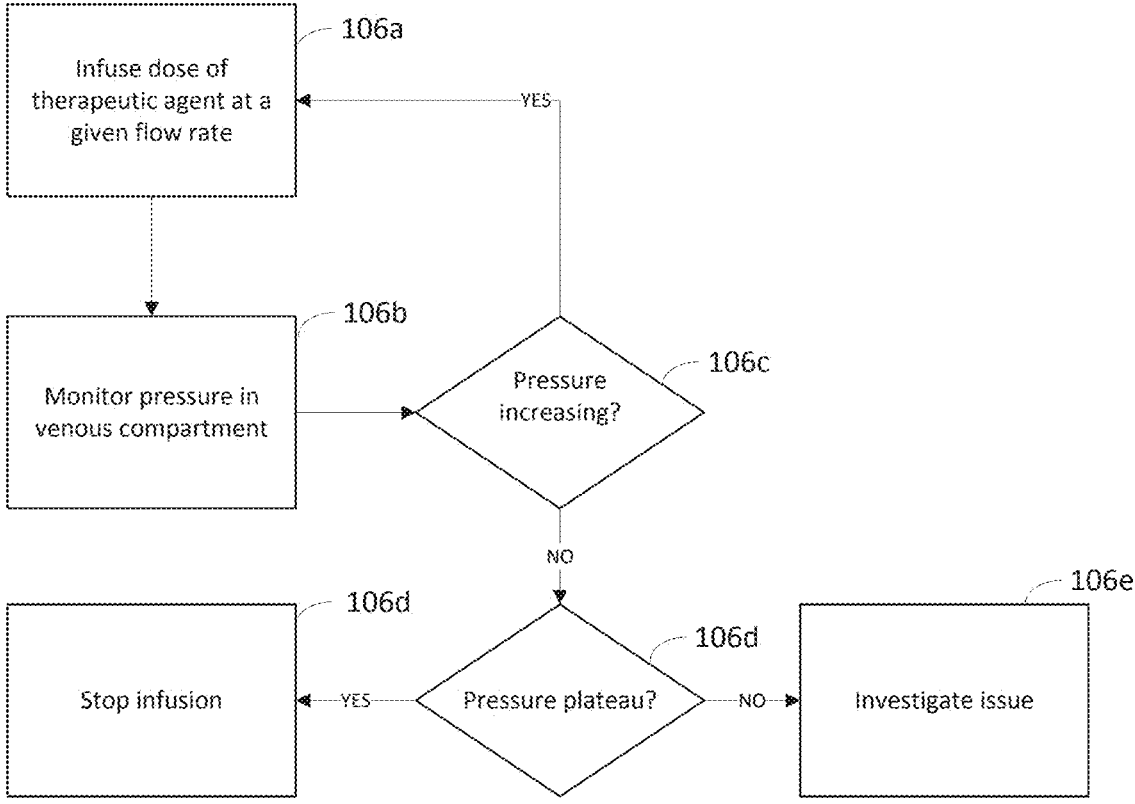
FIG. 6A is a flow chart of a method of using the system described herein.

In an alternative method to therapeutic infusion 106, the therapeutic agent is infused according to steps set forth in FIG. 6A. The therapeutic agent is infused 106a at a given infusion rate while the pressure in the venous compartment is monitored over time at 106b. A gradual increase in pressure at 106c is indicative of the fluid resistance resulting from displacing the blood within the venous compartment with the therapeutic agent as a larger volume of tissue is perfused in a retrograde manner. Increasing fluid resistance, as indicated by an increase in measured pressure over time, plateaus when alternative low resistance pathways are reached, with excess volume flowing to non-target arterial branches on the arterial side of the blocked vascular network. Thus, once the measured pressure stabilizes at a given infusion rate, such is an indication at 106d that there is full perfusion of the venous volume with the therapeutic agent. When the system reads that pressure has stabilized, a signal is then sent, e.g., to a controller for an infusion pump, to terminate infusion of the therapeutic agent at 106e. Finally, should the system read that pressure decreases at 106f during infusion, the issue should be investigated to determine the cause.

Returning to FIG. 6, once the therapeutic agent is delivered into the venous compartment, the therapeutic agent is permitted to dwell within the venous compartment for a period of time (dwell time). To effect the dwell, the occluder is left in the expanded configuration within the vessel. The dwell time can be determined by a dwell function, dependent upon parameters that permit optimum diffusion of the therapeutic agent across the vessel wall. For example, the dwell function can depend on the therapeutic agent (e.g., size of the molecule and molecular interaction with the vessel wall) and the measured pressure gradient. Holding other parameters constant, the larger the measured pressure gradient, the less time is required for optimal diffusion of the therapeutic agent into the tissue. The dwell time for a therapeutic solution maximizes the time in which the therapeutic solution resides within the target vasculature or, in other words, provides guidance for leaving the occluder open until the concentration of therapeutic agent in the blood of the vessel approaches zero and the concentration of the therapeutic agent in the surrounding target tissue increases to maximum availability from the dose. As the occluder blocks blood flow, this time is dependent upon the metabolic requirements of the tissue. In most cases the occluder may remain in place for up to 30 minutes before ischemic damage occurs to the tissue. This duration may be increased by the use of infusates that partially or totally replace the oxygen and/or nutrient requirements of the target tissues. By way of example, such infusates include oxygenated saline or phosphate buffered solutions, Ringer's solutions, cellular growth mediums such as RPMI, MEM (minimal essential media), and DMEM, and intravenous sugar solutions such as 5% dextrose solution. Baring the metabolic needs of the surrounding tissue, the diffusion rate of the therapeutic molecule as predicted by molecular mass and positive pressure gradient measurements from the pressure sensor can be used to calculate therapeutic diffusion depth for a given dwell time. As capillaries typically reside no further than 100 μm from a given volume of tissue, the dwell time can be calculated to ensure full penetration of the therapeutic agent to this depth.

A typical diffusion rate for a small molecule is on the order of 0.2-1 μm/sec at physiological pressure differentials of 10-30 mmHg from the vessel to surrounding tissue, allowing the molecule to diffuse through the 100 μm tissue volume in 2-8 minutes. Higher molecular weight biological protein-based agents have much lower diffusion rates on the order of 0.0002 μm/sec at physiological pressure differentials of 10-30 mmHg, resulting in a diffusion time of 60 minutes to fully penetrate a 100 μm tissue volume. As the pressure differential increases, the rate of diffusion increases.

Various models can be used to calculate the diffusion rate of a molecule through the tissue. Most such models are based around Fick's law of diffusion in which diffusion occurs in response to a concentration gradient expressed as the change in concentration due to a change in position. The local rule for molecular movement or flux J is given by Fick's 1st law of diffusion:

$$J = -\chi \frac{\partial c}{\partial x},$$

in which the flux J [cm$^{-2}$ s$^{-1}$] is proportional to the diffusivity $\chi$[cm$^2$/s] and the negative gradient of concentration, $$\frac{\partial c}{\partial x}[\text{cm}^{-3}\ \text{cm}^{-1}]\ \text{or}\ [\text{cm}^{-4}].)$$

Then, the distance of molecular penetration can be estimated by considering steady-state transport in one spatial dimension, wherein c(x) is concentration as a function of distance x, c(0)=c$_0$ is the source concentration, and x is the distance from the source, such that c→0 as x→∞. Assuming first order uptake kinetics, with an uptake rate of k$_u$c, then for diffusion-dominated transport, $$c = c_0^{\left(\frac{-x}{d_p}\right)},\ \text{where}$$

$$d_p = \left(\frac{D}{k_u}\right)^{\frac{1}{2}}$$

where, D is the diffusivity and d$_p$ is the characteristic penetration distance. It is calculated how long it takes for the concentration (c$_o$) to approach 0, i.e., such that the therapeutic agent has diffused out of the vessel and into the surrounding tissue. Thus, the diffusive transport can be used to calculate a transport rate of the therapeutic agent and determine, in whole or in part, the consequent dwell time at which the occluder is to remain in an open expanded configuration post-infusion to block venous flow while the therapeutic agent undergoes uptake into the target tissue.

It is also known that transport of molecules can be affected by pressure gradients. For convection-dominated transport with first-order kinetics based on the pressure differential between the vessel and the interstitial tissue, the equation can be applied with dp=u/ku, where u is the fluid velocity. As before, it is calculated how long it takes for the concentration (c$_o$) to approach 0, i.e., such that the therapeutic agent has diffused out of the vessel and into the surrounding tissue. Thus, the measured pressure gradient (difference from pressures measured at 106 and 102) can be used to calculate a transport rate of the therapeutic agent and determine, in whole or in part, the consequent dwell time at which the occluder is to remain in an open expanded configuration post-infusion for appropriate therapeutic agent uptake into the target tissue.

Other factors such as the osmotic pressure can also be considered, measured, evaluated, modified, and used to determine a transport rate of the therapeutic agent and calculate, in whole or in part, the consequent dwell time at which the occluder is to remain in an open expanded configuration post-infusion for appropriate therapeutic uptake into the target tissue.

In order to affect osmotic pressure, the salt balance of the solute that carries the therapeutic agent can be modified to affect the rate and extent at which the therapeutic agent diffuses by osmosis from the solution and is absorbed into the target tissue.

Referring back to FIG. 2, an analyte sensor 24 may be provided at the distal end of the tubular member 20 or on the occluder to sense at 116 the concentration of salts and/or therapeutic agents remaining in the therapeutic solution that is infused at the vascular compartment. The analyte sensor may likewise be provided to the balloon occluder embodiment shown in FIGS. 4 and 5.) For example, the analyte sensor 24 may be a resistivity sensor that can sense the salt balance of the solution in the vessel. As osmotic diffusion progresses, the concentration of salt within the solution normalizes to the salt concentration of the surrounding tissue. Such would register as a change in electrical resistance (i.e., a decrease in electrical resistance over time if the solution is starting as a low electrolyte solution; or an increase in electrical resistance over time if the solution is starting as a high electrolyte solution) as water and therapeutic agent would leach from the therapeutic agent solution into the surrounding tissue, thereby concentrating remaining salts in the solution. The clinical endpoint for delivery can be based on electrical resistivity associated with normalization to physiological salt concentration.

Referring to Fig. the analyte sensor 24 can also be a light sensor. The sensor 24 can be a single small fiberoptic cable that terminates at a similar location shown in FIG. 2, and can be used as an alternative to measuring the resistivity of the fluid in the venous compartment. The fiberoptic cable can transmit excitation light from an external light source 35 (which may be located on the handle 50 or elsewhere) to the distal end of the distal end of the fiber optic cable and which communicates with a sensor chip, also at 35.

This system can be used with (as described) and without other aspects of the system, such that it may be used in a system which does not include a pressure transducer, and can be used in any occlusive system, such as a balloon. In addition, the potentially extremely small size of a fiberoptic system for light emission and sensing allows the system to be made at relatively small size for traversing small vessels.

Alternatively (or additionally), the analyte sensor may be designed for a specific therapeutic compound. In such case the diffusion of the therapeutic agent can be monitored directly over time. The clinical endpoint for therapeutic delivery can be set based on the concentration of the therapeutic agent remaining in solution.

Thus, when using an analyte sensor, the dwell time is not necessarily a predetermined time but could be a length of time determined in real-time based on ongoing measurements from the analyte sensor; i.e., until the analyte sensor provides a reading indicating that the diffusion has reached an end-point in which sufficient therapeutic agent has been subject to tissue uptake.

In addition, it is contemplated that the factors such as diffusion, pressure gradient, osmotic pressure, and light absorption and/or emission may be used in combination of two or more to calculate a dwell time at which the occluder is to remain in an open expanded configuration post-infusion for appropriate therapeutic uptake into the target tissue. Once the dwell time is complete and the dose of agent has been delivered 114, therapeutic delivery is complete.

Figure 6B:
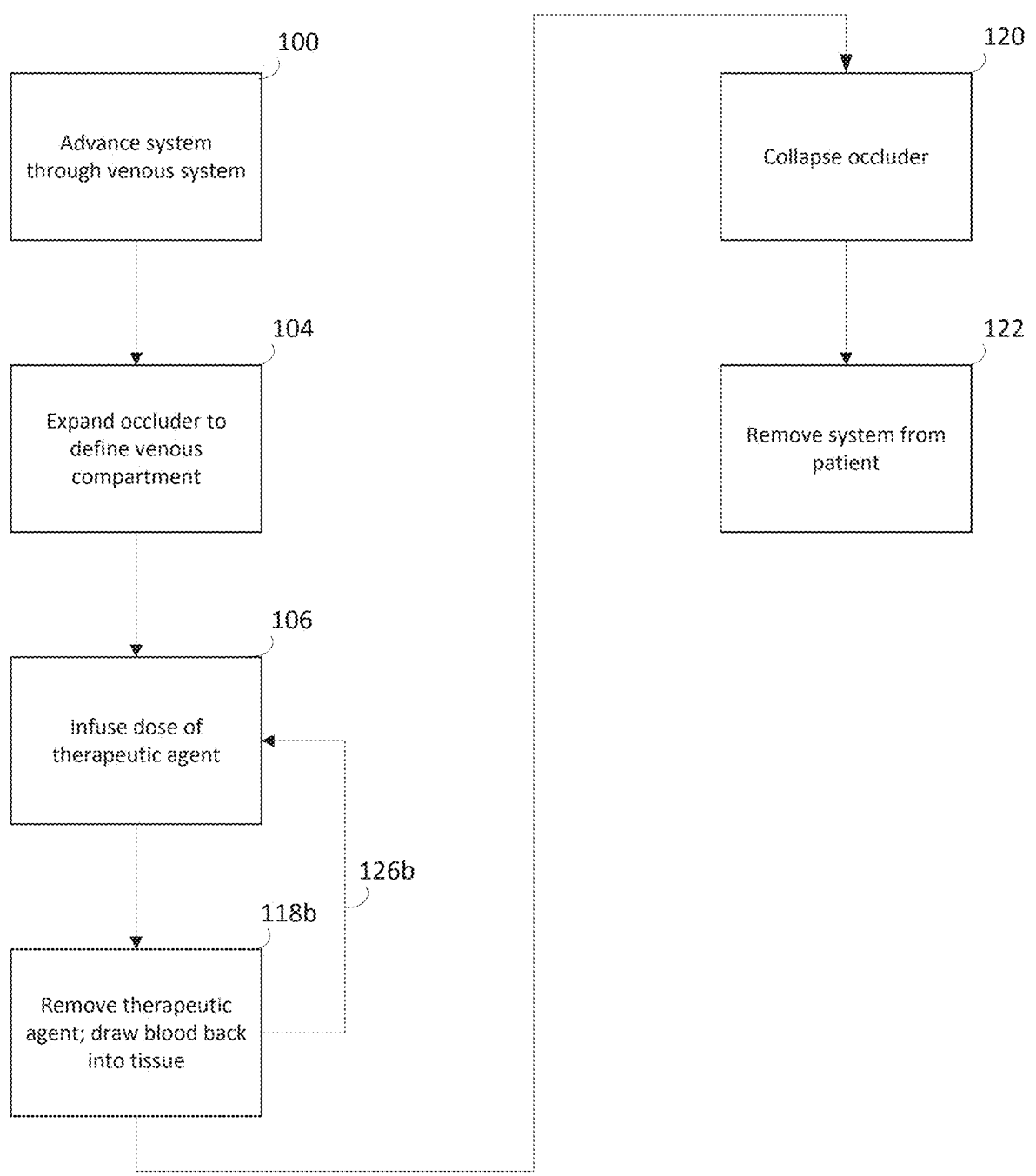
FIG. 6B is a flow chart of a method of using the system described herein.

Turning to FIG. 6B, in yet another alternative aspect of the method, after advancing the system 100, expanding the occluder 104, and infusing the therapeutic agent 106 (in combination with any or all of the other previously discussed steps to this point), rather than allow the therapeutic agent to statically dwell for a period of time within the venous compartment, the therapeutic agent is removed 118*b* and replaced with upstream blood, and then re-infused. The process of removal and re-infusion may be repeated multiple times in a pulsatile action 126*b*, as further described below. This process has certain therapeutic benefits.

Pressurized delivery can overcome resistance presented by solid tumor stress, high interstitial pressure, and dense interstitial matrix. An applied pressure differential in the vessel to the tumor during infusion of a therapeutic agent, e.g., 10-100 mmHg above local blood pressure, can facilitate penetration of the tumor with the therapeutic agent and lead to improved response rates from the therapy.

However, the maintenance of pressure in the vessel requires the presence of fluid flow. In applications where the target volume of tissue is small or the fluid volume of therapeutic agent is limited (such as in the limited venous compartment), maintenance of a therapeutically relevant pressure may be challenging. The limited fluid volume of the venous approach renders it impractical to perform continuous high flow rate infusion to generate pressure as the total duration of pressure generation (and thereby duration of increased tissue penetration) will be short. Moreover, it may be advantageous to limit the overall volume of a delivered therapeutic agent to prevent adverse impact on non-target tissues. That is, a large volume of therapeutic agent administered to a small volume of tissue to increase the duration of pressure generation would result in excess therapeutic agent migrating through the vascular network until an arterial branch occurs, allowing the balance of the therapeutic agent to enter systemic circulation through a collateral approach. It is therefore desirable to use only a sufficient volume of therapeutic agent required to fully perfuse the target tissue volume. Moreover, continuous infusion of therapeutic agent for a long duration may lead to tissue ischemia and/or clot formation if blood stagnation occurs.

Thus, in accord with an optional aspect of the method, the unique anatomy of the local venous approach is exploited to allow for continuous pulsatile pressurized administration of therapeutic. The system for such optional aspect of the method is shown in FIG. 1, and includes the occlusive system 10, the pressure monitor 23 coupled to the pressure transducer 22, the pump 25 operable in a reversible manner, the controller 27 operationally controlling the pump to infuse the therapeutic agent from the syringe 31 or other storage container at the flow rate, and optionally the timer 37. The timer 37 may be integrated within the controller 27. As an alternative to a reversible pump 25, two pumps may be provided: a first for pumping in a first direction, and a second for pumping in an opposite second direction.

The pressure monitor 23 monitors the pressure in the vessel. The controller 27 adjusts the flow of therapeutic agent by the pump 25. If the monitored pressure is below a predetermined pressure, a signal can be sent from the controller 27 to the pump 25 to increase the flow rate of infusion to thereby increase pressure in the vessel. Then, if the monitored pressure is above a predetermined pressure, a signal can be sent from the controller 27 to the pump 25 to decrease the flow rate of infusion to thereby decrease pressure in the vessel. The controller 27 detects when a fixed volume of therapeutic agent has been delivered from the pump 25 to the vessel. The fixed volume is predetermined by the physician as a volume required to perfuse the venous volume. When the fixed volume of therapeutic agent has been delivered, the controller 27 sends a signal for the pump 25 to stop infusion. Then, immediately afterwards or after a determined delay as controlled by the timer 37, the controller 27 switches the pump 25 to a withdrawal mode. In withdrawal mode, the pump 25 generates a vacuum that results in removal of the therapeutic agent from the venous volume back into the syringe 31 or other storage while simultaneously causing the therapeutic agent to be replaced by the blood that was displaced upstream. The rate of withdrawal is preferably determined by the physician in order to maintain pressure in the vessel (i.e., pressure of the baseline venous system). After the therapeutic agent is removed and replaced with blood, the removed therapeutic agent is again pumped by the pump 25 from its storage 31 back into the venous volume at a sufficient flow rate to generate a therapeutically relevant pressure until the fixed volume of therapeutic agent is delivered. The controller 27 is then operated to either immediately afterwards, or after a delay, to again remove the therapeutic agent. These cycles of high flow rate introduction and subsequent removal and replacement of the therapeutic agent with blood are repeated until a set duration of exposure time at a therapeutic relevant pressure or a determined number of cycles of pulsatile therapeutic delivery and removal of therapeutic agent is performed. By way of example only, the process may be performed two to twenty cycles, more preferably up to ten cycles, and even more optimally, up to seven cycles.

In one method, after completion of the delivery of the therapeutic agent, the proximal handle 50 is then actuated to collapse the occluder 20 at 120, and the system is then removed at 122 from the patient. Once the occluder is collapsed, blood flow is permitted to resume in an arterial-to-venous flow path through the venous volume; in such case, the remaining therapeutic agent in the venous volume is permitted to circulate systemically.

In another method, more applicable to delivery of the therapeutic dose in a single delivery into the controlled venous volume rather than via the above described pulsatile delivery, all or a portion of the therapeutic agent remaining (non-absorbed therapeutic agent) in the controlled venous volume is removed from the patient prior to collapsing the occluder and/or removing the system from the patient. In circumstances it may be suitable to aim to remove at least 50% of such remaining therapeutic agent; in circumstances it may be suitable to aim to remove at least 65%, or at least 70%, or at least 80%, or at least 90%, or up to 100% of such remaining, non-absorbed therapeutic agent in the venous volume; in circumstances it may be suitable to aim to a range of 50-100% of such remaining, non-absorbed therapeutic agent in the venous volume; or a range of 65-100% of such remaining, non-absorbed therapeutic agent in the venous volume; or a range of 70-100% of such remaining, non-absorbed therapeutic agent in the venous volume; or a range of 80-100% of such remaining, non-absorbed therapeutic agent in the venous volume; or a range of 90-100% of such remaining, non-absorbed therapeutic agent in the venous volume. Methods described herein can be adjusted to meet at least an intended minimum required recovery of non-absorbed therapeutic.

While the therapeutic agent can be removed via any pathway, it is preferable that the therapeutic agent be removed via a reverse, parallel path to its infusion, such as through the infusion lumen 18 of the catheter or another lumen co-axial or parallel to the infusion lumen. Thus, in a preferred method, it is appreciated that the removal of the solution occurs through the same vessels through which the solution was injected. The solution can be withdrawn via effecting a reduced pressure at the removal lumen relative to pressure in the occluded venous volume.

Poiseuille's Law identifies the relationship between horizontal flow rate within a tube and the pressure and resistance within a tube. For a pressure differential between two locations in a tube (P1 and P2), and a resistance to flow between those locations (R) in the tube, the flow rate equals:

$$Q = \frac{P_2 - P_1}{R}.$$

The resistance R includes everything, except pressure, that affects flow rate. For example, R is greater for a long tube than for a short one. The greater the viscosity of a fluid, the greater the value of R. Turbulence greatly increases R, whereas increasing the diameter of a tube decreases R. The resistance R to laminar flow of an incompressible fluid having viscosity $\eta$ through a horizontal tube of uniform radius r and length l, is given by Poiseuille's law for resistance:

$$R = \frac{8\eta l}{\pi r^4}.$$

Taken together, the equation for laminar flow rate within a tube such as a lumen of catheter is:

$$Q = \frac{(P_2 - P_1)\pi r^4}{8\eta l}.$$

Thus, the rate of removal of therapeutic agent can be modified by adjusting the relative pressure differential and the diameter of the evacuation lumen. By way of example, it may be intended to remove 10 cc of therapeutic agent when a relative negative pressure of 100 mmHg is applied to the evacuation lumen at the exterior hub coupled to the catheter. In one example, it is intended to remove the therapeutic agent within 60 seconds; to achieve this rate, a lumen with an inner diameter of 0.027 inch is used. In a second example, it is intended to remove the therapeutic agent within 120 seconds; to achieve this rate, a lumen with an inner diameter of 0.019 inch is used. In a third example, it is intended to remove the therapeutic agent within 30 seconds; to achieve this rate, a lumen with an inner diameter of 0.038 inch is used. The rate of flow through the evacuation lumen is shown on the display of the handle 50.

Figure 7:
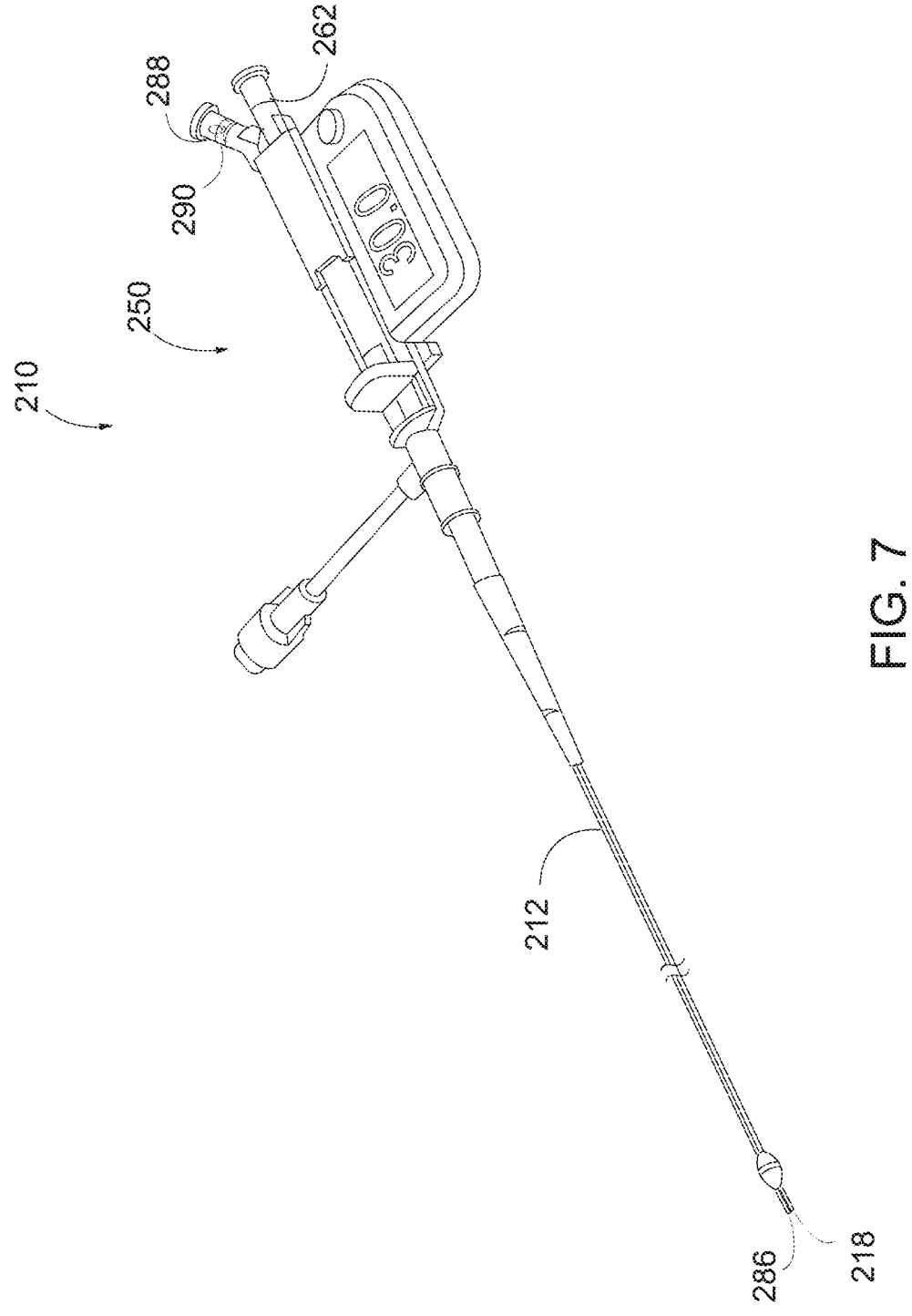
FIG. 7 is a perspective view of another occlusion system for use in a method described herein.

Alternatively, referring to FIG. 7, the system 210 can include a multi-lumen catheter 212 with an infusion lumen 218 and a separate evacuation lumen 286 through which the solution can be aspirated or otherwise evacuated from the patient. The evacuation lumen 286 extends parallel to the infusion lumen 218. The infusion lumen 218 and evacuation lumen 286 extend side-by-side, as shown, or may be coaxial with each other. The handle 250 includes ports 262, 288 for the respective infusion and evacuation lumens. The design of the evacuation lumen 286 can likewise be adjusted in diameter to facilitate removal of the intended therapeutic in a given timeframe for a given volume and pressure differential. The evacuation lumen can be set as the same diameter as the infusion lumen. Alternatively, the evacuation lumen can have a diameter different from the diameter of the infusion lumen; such diameter may be fixed or variable. The evacuation lumen 286 at the port 288 is provided with a valve 290 with an adjustable variable size opening or constriction, e.g., in the form of a mechanical iris, adapted to control the rate of passage of fluid out of the evacuation lumen.

To further adjust the rate of removal, the negative pressure applied to the evacuation lumen can be adjusted. The negative pressure may be a differential between an ambient pressure that is less than the fluid pressure within the occluded venous volume and the fluid pressure within the occluded venous volume. In another embodiment, the negative pressure may be generated by a vacuum element. The negative pressure can be a partial vacuum. A suitable pressure may be achieved by a pressure at one atmosphere, or any pressure less than one atmosphere of pressure, as the occluded venous volume will be pressurized by the arterial side pressure of the occluded blood volume. The vacuum element may be passive, manually actuated, or active. Referring to FIGS. 7 and 8, in a passive system, the vacuum element can be a container 300 retaining a vacuum of fixed volume 302 which can be coupled to the exterior connector 288 of the evacuation lumen 286. The container 300 includes a seal, such as a pierceable septum 304, that holds the vacuum in the container. The exterior connector 288, for coupling with the container 300, preferably is adapted to receive, pass through, or otherwise engage a mouth 306 or other opening of the container to access the volume 302 under vacuum. The container and/or connector may include luer connectors 308, 310 for secure connection to each other. Referring to FIG. 9, when the container 300 is coupled to the connector, the seal 304 is penetrated to access the volume 302 under vacuum and the therapeutic agent solution 312 is drawn into the container in the direction of arrow 314. Removal of the therapeutic agent solution may be complete when the volume in the container is filled with aspirated therapeutic agent solution. Alternatively, removal of the therapeutic agent solution may be considered complete when the volume in the container is partially filled with aspirated therapeutic agent solution. In yet another alternative, removal of the therapeutic agent solution may be considered complete when multiple containers are filled or partially filled with aspirated therapeutic agent solution. It is recognized that this mode of evacuation/aspiration may be combined with a container provided with separate volume of a deliverable quantity of the therapeutic agent, such that the agent delivery and solution recovery containers are a common system. Thus, a single disposable device can be used for containing the therapeutic agent prior to delivery to the patient and disposal of the solution after delivery to the patient.

Turning now to FIGS. 10 and 11, one embodiment of an integrated container 700 with a first volume 702 with a stored therapeutic agent 704, and a second volume 706 having (or adapted to generate) a vacuum 708 for subsequent therapeutic agent aspiration into the second volume. A proximal end 710 or any side of the first volume 702 includes a connector 712 for connection with a pressure generator such as a syringe filled with an incompressible fluid, such as saline (not shown). The connector 712 may be a luer connector. Alternatively, the first volume 702 may be sealed at a predetermined pressure exceeding atmospheric pressure and fluid pressure within the occluded venous volume of the patient such that the therapeutic agent is charged to be infused into a patient without additional pressure generation.

The distal end 714 of the container 700 includes a mating connector 716 for removable connection to a hub connector 62 on the handle of the delivery system 10 (see FIG. 1). Internally, the mating connector 716 includes respective pierceable septa 720, 722 that seal the first and second volumes 702, 706. The proximal end of the catheter is coupled with a hollow needle 724 and gasket 726. The needle 724 provides fluid communication to the infusion lumen 18 of the catheter 12 (see also FIGS. 1 and 2). A button 728 accessible from outside the hub connector 62, is coupled to the needle 724, and can be moved through a track 730 into discrete locations to cause the gasket 726 to seal against a respective septa 720, 722, and the needle 724 to pass through a respective one of the septa into fluid communication with an interior of one of the first and second volumes 702, 706 at a time. When the button 728 is positioned to move the needle 724 into communication with the first volume 702, the therapeutic agent 704 is ready to be infused through the infusion lumen 18. Alternatively, when the button 728 is positioned in the track 730 to move the needle 724 into fluid communication with the second volume 706, the vacuum in the second volume is adapted to draw fluid through the infusion lumen 18 and into the second volume. The button may have positive locks in the track, e.g., travel in a direction, exemplified by arrow 732, that prevents movement toward fluid communication between the needle and the other volume, as exemplified by arrow 734. The container 700 is adapted to both infuse therapeutic agent into the patient and evacuate therapeutic agent back into the container from the patient without removing the container from the handle hub 18.

Figures 12, 13:
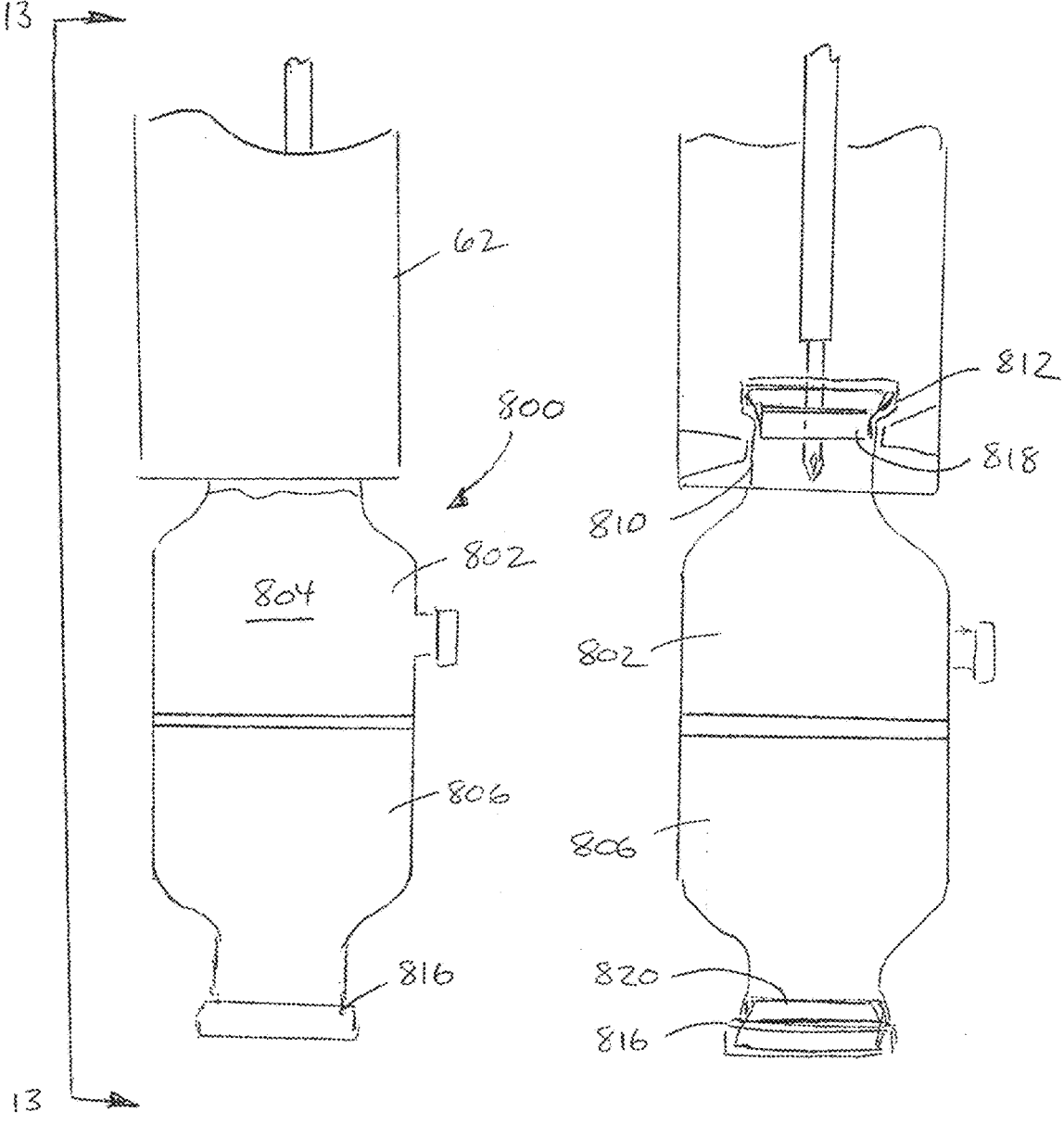
FIG. 12 is a schematic view of an embodiment of an integrated therapeutic agent delivery and retrieval device and a portion of a hub connector of a handle of a catheter delivery system.
FIG. 13 is a schematic view along line 13-13 in FIG. 12.
Figures 14, 15:
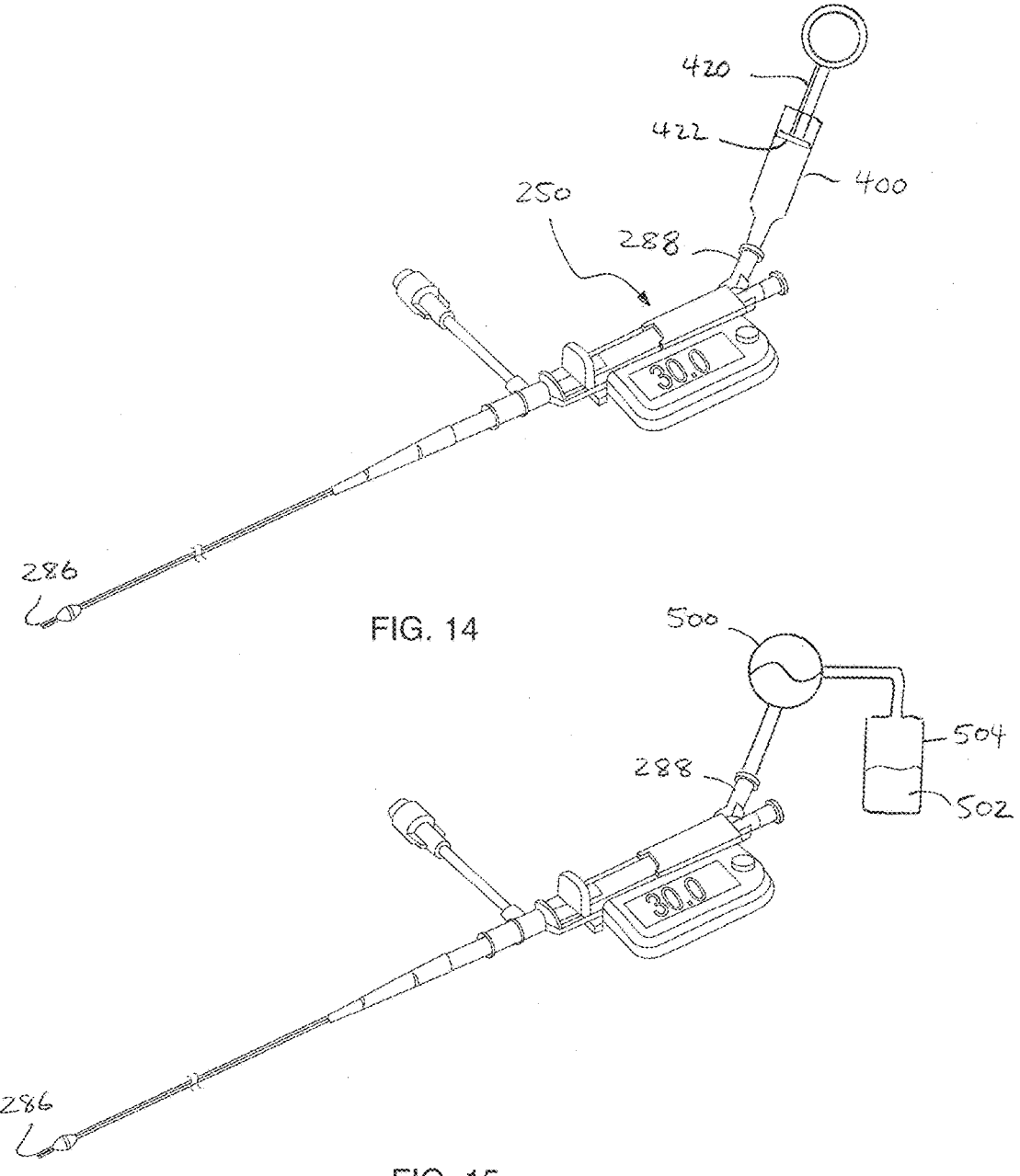
FIG. 14 shows a passive adjustable variable volume vacuum container for removal of therapeutic agent solution from a patient.
FIG. 15 shows an active vacuum system for removal of therapeutic agent solution from a patient.

Turning now to FIGS. 12 and 13, another embodiment of an integrated container 800 with a first volume 802 with a stored therapeutic agent 804, and a second volume 806 having (or adapted to generate) a vacuum 808 for subsequent therapeutic agent aspiration into the second volume. The container 800 has a first end 810 defining a first connector 812 for placing the first volume 802 in fluid communication with the infusion lumen 18 through hub connector 62 (FIGS. 1 and 2), and a second end 814 defining a second connector 816. Each of the first and second connectors 812, 816 includes a respective septum 818, 820 that maintains a seal on the respective first and second volumes 802, 806 unless and until the septum is pierced. Seals other than pierceable septa can similarly be used. In distinction from the container described at 700, container 800 is coupled to the hub connector 62 to infuse therapeutic agent through the infusion lumen 18 into the patient, then decoupled and re-oriented, and then re-coupled to the hub connector 62 for evacuation of the therapeutic agent back into the container (FIG. 1). Referring to FIG. 14, in another example, a separate vacuum container (or separate vacuum volume of an integrated disposable device) 400 may comprise a variable displacement device attached to evacuation lumen 286 of the catheter. The vacuum container may comprise a manually actuatable syringe 400 including a piston 420 with a seal 422 displaceable away from a dead space position near the connector 288 on the handle 250 to generate negative pressure. The piston 420 may be moved and fixed at a location in the container to define a desired interior volume under negative pressure. The fixing may occur as a result of friction between the seal and interior container wall, other friction mechanism or interference, or a mechanical lock. Removal of therapeutic agent solution is complete when the defined volume of the container has been filled by the aspirated therapeutic agent solution.

In yet another example, referring to FIG. 15, a separate vacuum element (or separate vacuum volume of an integrated disposable device) 400 can integrate an active pump 500, such as a impeller fluid pump, coupled to the connector 288 and applying a vacuum pressure to the evacuation lumen 286 when the pump is activated. The pump 500 moves the aspirated therapeutic solution 502 to a disposal chamber 504. The magnitude of the pressure differential generated by the vacuum element impacts the rate at the therapeutic agent solution is remove from the patient. In a first example, 10 cc of therapeutic agent solution is removed through a catheter with a lumen inner diameter of 0.027 inch within 60 seconds when a negative pressure of 100 mmHg is applied at the connector 62 of the handle 50. In a second example, 10 cc of therapeutic agent solution is removed through a catheter with a lumen inner diameter of 0.027 inch within 30 seconds when a negative pressure of 200 mmHg is applied at the connector.

In addition, the device may be adapted to determine and notify a user when the withdrawal of the therapeutic agent solution is complete. In one example, the analyte sensor 24 of the device senses and monitors the conductance or resistivity of the withdrawn of the fluid during extraction. When a conductance shift occurs as a result in difference in conductivity between the therapeutic agent solution and the blood, either the application of negative pressure is automatically stopped, or the user is notified to end withdrawal. Notification is made via a text on the display of the handle, light, other visual cue, a sound, a vibration, or automatically stopping the evacuation of fluid.

Figure 16:
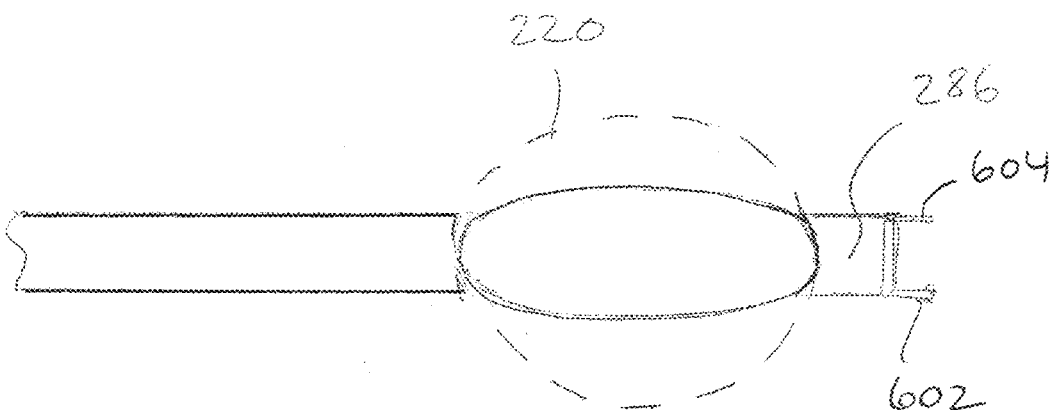
FIG. 16 is an enlarged distal end view of an embodiment of an occlusion system illustrating a light detector system.

In another example, referring to FIG. 16, the system is provided with a light emitter 602 and a light sensor 604 near a distal orifice of the evacuation lumen 286 (on the distal side of the occluder 220). The light emitter and sensor may operate in the infrared (wavelengths generally greater than 2500 nm), near-infrared (wavelengths generally in the range of 650-2500 nm), visible spectrum (wavelengths generally in the range of 380 to 700 nm), ultraviolet (wavelengths generally in the range of 100-400 nm), X-ray, or other electromagnetic wavelengths adapted for sensing the presence of the therapeutic agent or associated tracer molecules. The light emitter may generate light from a source near the opening of the evacuation lumen; alternatively, the light emitter may be a fiber optic carrying light from a light source outside the patient. The light sensor may be a light intensity sensor. The light sensor may be an IC chip located outside the patient and have light carried to it from the distal end of the fiber optic. The light emitter and light sensor may be used together to measure light transmitted through the vessel during withdrawal of the therapeutic agent solution. As blood is a translucent fluid, a portion of the light emitted by the emitter is blocked by the blood on its way to the light intensity sensor. The blood, when fully or partially replaced by the therapeutic agent solution has different translucency. The change in translucency monitored by the light intensity sensor as the therapeutic agent solution is withdrawn and the ratio of fluid in the vessel changes from a lower concentration of blood and higher concentration of therapeutic agent solution to a higher concentration of blood and lower concentration of therapeutic agent solution is used to determine an endpoint to the aspiration. The light sensor may also be a light spectral detector that monitors for one or more specific light frequency or frequencies or range of frequencies that is/are absorbed by the drug; i.e., a spectral shift in the light received by the detector after the light passes through the therapeutic agent solution. Such detected light has different detected color and/or absorbance properties when passing through the therapeutic agent solution and the blood. Thus, the unique spectral signature of the therapeutic agent solution can be detected Such detection allows for complete (or near complete) removal of remaining therapeutic agent solution even in the presence of blood.

The sensor system may also include a combination of two or more of the described analyte sensor, light emitter and light sensors, and a resistivity sensor. Other sensors can also be used alone or in combination to sense a characteristic of the solution in the vessel and determine its concentration in the vessel. The readings of the combined sensors system can more accurately define an endpoint for completion of therapeutic solution removal.

In all methods where the solution is removed at the end of the dwell time, it is preferably removed through a reverse pathway, in distinction from circulating the solution further through the other vessels and/or tissue.

There have been described and illustrated herein embodiments of systems and methods for intravascular delivery of a therapeutic agent through a vessel to a tissue, such as an organ. While particular embodiments of the invention have been described, it is not intended that the invention be limited thereto, as it is intended that the invention be as broad in scope as the art will allow and that the specification be read likewise. Thus, it is recognized that the systems and methods may be applied to both humans and animals. Also, while examples of organs and disease states have been provided, such lists are not meant to be exclusive and the systems and methods are intended to be used where ever they would have therapeutic utility, in association with any such organs, disease states, and with any appropriate therapeutic agents now known or hereinafter discovered or developed. Also, the flexible tubular member can be any catheter arrangement meeting the needs of the device claimed, i.e., permitting passage of the therapeutic agent and actuation of the occluder, and, in embodiments hereof, evacuation of the therapeutic agent therethrough. Further, while several preferred occluders have been described, any suitable vascular occluders may be used as well to assemble the systems and accomplish the methods described herein. Also, while several pressure sensor systems, sensors for characterizing the therapeutic agent in vivo, such as in terms of a quality and/or a quantitative relationship either alone or compared to an in vivo occluded store of venous blood, methods for determining dwell time, and systems and methods removing therapeutic agent solution, and systems and methods for determining once sufficient solution has been removed are described, it is intended that any single one of these single or a combination of any two or more these systems can be used to provide targeted therapeutic agent delivery and/or partial or full therapeutic agent solution removal from a patient. It will therefore be appreciated by those skilled in the art that yet other modifications could be made to the provided invention without deviating from its scope as claimed.

What is claimed is:

1. A system for temporarily occluding a target vessel in a patient during infusion of a solution of a therapeutic agent to the patient, comprising:

a) a flexible inner tubular member comprising a proximal end, a distal end, and an infusion lumen extending between the proximal and distal ends, the infusion lumen opening to a distal orifice at the distal end of the flexible inner tubular member;

b) an outer catheter comprising a proximal end, a distal end, and a flush lumen defined between the flexible inner tubular member and the outer catheter, the flush lumen opening to a distal aperture at the distal end of the flush lumen;

c) an expandable occluder at the distal end of the outer catheter, the expandable occluder having a collapsed configuration for advancement through the target vessel and an expanded configuration for occluding the target vessel, wherein the expandable occluder is proximal of the distal orifice of the flexible inner tubular member;

d) a pressure sensor in fluid communication with the flush lumen, the pressure sensor configured to sense, with a delay in response time, in vivo fluid pressure distal of the expandable occluder, wherein the pressure sensor is located proximal of the distal aperture at a distance such that the delay in response time is suitably short for the pressure sensor to monitor pressure changes during the infusion of the solution, the delay in response time corresponding to a cross-sectional area of the flush lumen and the distance between the pressure sensor and the distal aperture; and e) a delivery system comprising a controller and an infusion pump, the delivery system configured to deliver the solution of the therapeutic agent at an infusion rate through the infusion lumen of the flexible inner tubular member and to the target vessel until the pressure sensor senses that the fluid pressure distal of the expandable occluder has stabilized, wherein the delivery system allows the solution of the therapeutic agent to dwell within the target vessel for a period of a dwell time after infusion while the expandable occluder remains in the expanded configuration, wherein the controller determines the dwell time as a function of a pressure differential between a first pressure distal of the expandable occluder sensed by the pressure sensor when the expandable occluder is in the collapsed configuration, and a second pressure distal of the expandable occluder sensed by the pressure sensor when the expandable occluder is in the expanded configuration.

2. The system of claim 1, further comprising f) a fluid evacuation system to remove at least a portion of the delivered solution of the therapeutic agent from the patient through an evacuation lumen while the expandable occluder is in the expanded configuration.

3. The system of claim 1, wherein the controller determines the dwell time as a period for the solution to dwell in the vessel that optimizes filtration of the therapeutic agent from the solution into a target tissue based on the pressure differential between the first and second pressures distal of the expandable occluder sensed by the pressure sensor.

4. The system of claim 1, wherein the sensor is located from 50 cm to 100 cm away from the distal aperture of the flush lumen.

5. The system of claim 1, wherein the cross-sectional area of the flush lumen is 0.5 mm$^2$ and the delay in response time of the sensor is 2-5 seconds.

6. The system of claim 1, wherein the cross-sectional area of the distal aperture of the flush lumen is 0.5 mm$^2$ and the delay in response time of the sensor is 1-3 seconds.

7. The system of claim 1, wherein the cross-sectional area of the flush lumen is 2 mm$^2$ and the delay in response time of the sensor is 0.1-0.5 seconds.

8. The system of claim 1, wherein the pressure sensor is configured to continually sense, with the delay in response time, the in vivo fluid pressure distal of the expandable occluder.

9. The system of claim 1, wherein the expandable occluder comprises an inflatable occlusion balloon and the sensor is in pressure communication with a distal side of the inflatable occlusion balloon.

10. The system of claim 1, wherein the expandable occluder comprises a microvalve comprising a proximal end coupled to the distal end of the outer catheter, a distal end coupled to the distal end of the flexible inner tubular member, a fluid permeable coating over a distal portion of the expandable occluder.

11. The system of claim 10, wherein the fluid permeable coating membrane comprises pores configured to dampen pressure fluctuations sensed by the pressure sensor and the response time of the sensor is 0.2-1 seconds.

12. The system of claim 10, wherein the pores are configured to dampen pressure fluctuations sensed by the pressure sensor and the response time of the sensor is 0.01-0.2 seconds.

13. The system of claim 1, further comprising a side port in fluid communication with the flush lumen, wherein the sensor is located at the side port.

14. The system of claim 1, wherein the delay in response time is at or less than 5 seconds.

15. The system of claim 1, wherein the controller determines the dwell time as a period for the solution to dwell in the vessel that optimizes diffusion of the therapeutic agent from the solution across a wall of the target vessel.

\* \* \* \* \*